United States Patent
Cleek et al.

(10) Patent No.: US 10,688,188 B2
(45) Date of Patent: Jun. 23, 2020

(54) POLYTETRAFLUOROETHYLENE CO-POLYMER EMULSIONS

(71) Applicant: W. L. Gore & Associates, Inc., Newark, DE (US)

(72) Inventors: Robert L. Cleek, Flagstaff, AZ (US); Edward H. Cully, Flagstaff, AZ (US); Paul D. Drumheller, Flagstaff, AZ (US); Theresa A. Holland, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/371,257

(22) Filed: Apr. 1, 2019

(65) Prior Publication Data
US 2019/0224323 A1 Jul. 25, 2019

Related U.S. Application Data

(63) Continuation of application No. 16/123,614, filed on Sep. 6, 2018, which is a continuation of application No. 14/025,708, filed on Sep. 12, 2013, now Pat. No. 10,092,653.

(60) Provisional application No. 61/780,913, filed on Mar. 13, 2013, provisional application No. 61/700,842, filed on Sep. 13, 2012.

(51) Int. Cl.
| | | |
|---|---|---|
| A61K 47/32 | (2006.01) | |
| A61K 49/04 | (2006.01) | |
| A61L 27/34 | (2006.01) | |
| A61L 27/54 | (2006.01) | |
| A61L 29/08 | (2006.01) | |
| A61L 29/16 | (2006.01) | |
| A61L 17/14 | (2006.01) | |
| C09D 131/04 | (2006.01) | |
| A61K 9/107 | (2006.01) | |
| A61L 31/10 | (2006.01) | |
| A61L 31/16 | (2006.01) | |
| A61K 9/10 | (2006.01) | |
| A61K 47/30 | (2006.01) | |
| A61B 17/12 | (2006.01) | |

(52) U.S. Cl.
CPC ........... *A61K 47/32* (2013.01); *A61K 9/107* (2013.01); *A61K 49/04* (2013.01); *A61L 17/145* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C09D 131/04* (2013.01); *A61B 17/12181* (2013.01); *A61K 9/10* (2013.01); *A61K 47/30* (2013.01); *A61L 2300/802* (2013.01); *A61L 2420/00* (2013.01); *A61L 2420/02* (2013.01); *A61L 2420/04* (2013.01); *A61L 2420/06* (2013.01); *A61L 2430/36* (2013.01)

(58) Field of Classification Search
None
See application file for complete search history.

(56) References Cited

U.S. PATENT DOCUMENTS

| | | |
|---|---|---|
| 5,188,890 A | 2/1993 | Ohashi et al. |
| 8,048,442 B1 | 1/2011 | Hossainy |
| 8,048,440 B2 | 11/2011 | Chang et al. |
| 8,609,125 B2 | 12/2013 | Chang et al. |
| 10,092,653 B2 | 10/2018 | Cleek |
| 2004/0063805 A1 | 4/2004 | Pacetti |
| 2005/0106204 A1 | 5/2005 | Hossainy |
| 2006/0198866 A1 | 9/2006 | Chang |
| 2008/0254094 A1 | 10/2008 | Martel et al. |
| 2009/0053391 A1 | 2/2009 | Ludwig |
| 2010/0121421 A1 | 5/2010 | Duncan |
| 2011/0064781 A1 | 3/2011 | Cleek et al. |
| 2011/0098797 A1 | 4/2011 | Cleek |
| 2014/0072518 A1 | 3/2014 | Cleek |

FOREIGN PATENT DOCUMENTS

| | | |
|---|---|---|
| JP | 2011512346 A2 | 8/2009 |
| JP | 2011-512346 | 4/2011 |
| WO | WO-2004026359 A1 | 4/2004 |
| WO | WO-2009053391 A1 | 4/2004 |
| WO | WO-2009101263 A2 | 2/2009 |
| WO | WO-2009045423 A1 | 4/2009 |
| WO | WO-2011035001 A2 | 3/2011 |

OTHER PUBLICATIONS

Baradie, B and Shoichet, M. S. Synthesis of Fluorocarbon—Vinyl Acetate Copolymers in supercritical Carbon dioxide: Insight into Bulk Properties. Macromolecules 2002, 35, p. 3569-3575.
European Search Report from EP13765925.6, dated Apr. 26, 2018, 5 pages.
International Search Report and Written Opinion from PCT/US2013/059787, dated Mar. 21, 2014, 23 pages.

*Primary Examiner* — James W Rogers

(57) ABSTRACT

The present disclosure is directed to a class of fluorinated copolymers, such as PTFE copolymers, that can be dissolved in low toxicity solvents, such as Class III Solvents, and that enable the creation of stable water-in-solvent emulsions comprising the fluorinated copolymers dissolved in a low toxicity solvents and a hydrophilic agent (e.g., a therapeutic agent) dissolved in an aqueous solvent, such as water or saline.

7 Claims, 14 Drawing Sheets

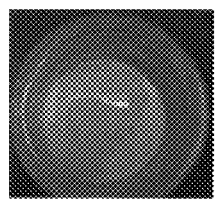 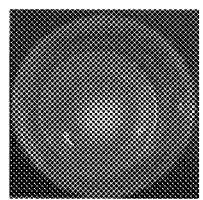 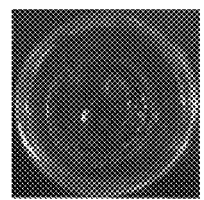 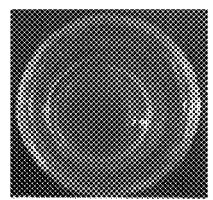
FIG. 4(a)   FIG. 4(b)   FIG. 4(c)   FIG. 4(d)
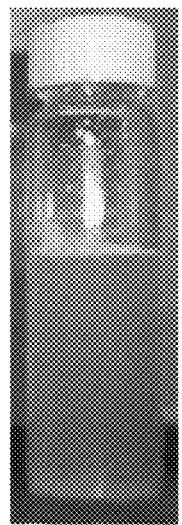 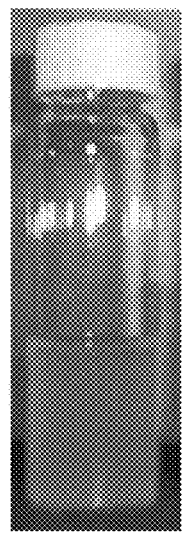 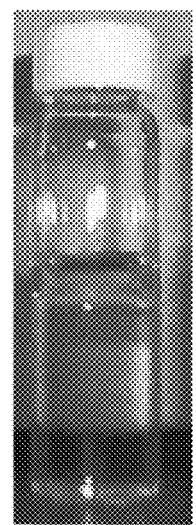 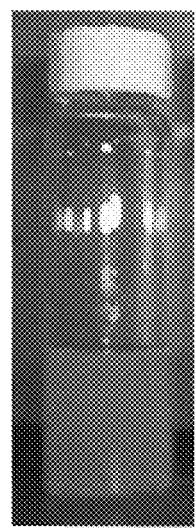
FIG. 5(a)(i)   FIG. 5(b)(i)   FIG. 5(c)(i)   FIG. 5(d)(i)
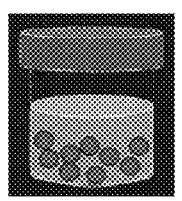 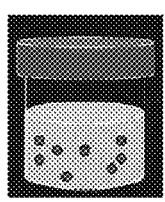 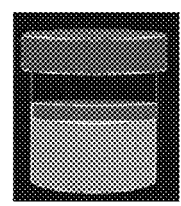 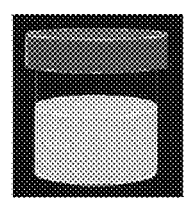
FIG. 5(a)(ii)   FIG. 5(b)(ii)   FIG. 5(c)(ii)   FIG. 5(d)(ii)

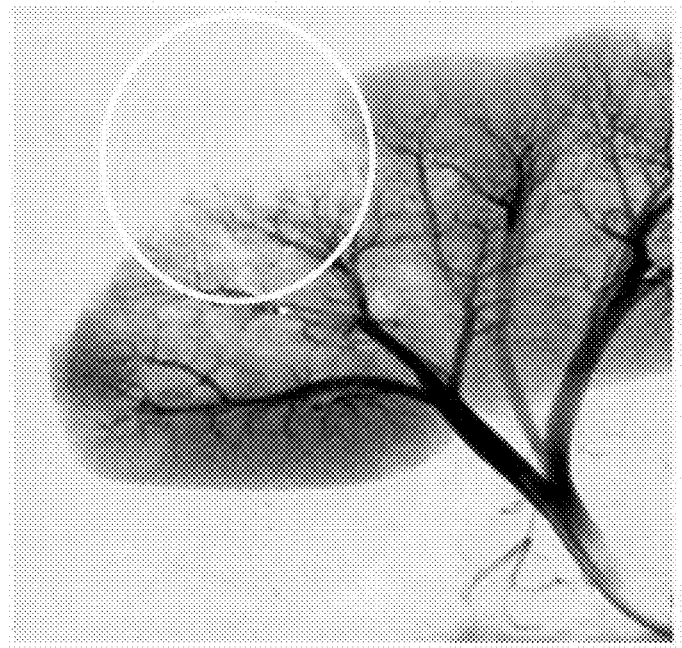
FIG. 9(b) Porcine kidney post-embolization
FIG. 9(a) Porcine kidney pre-embolization

POLYTETRAFLUOROETHYLENE CO-POLYMER EMULSIONS

CROSS-REFERENCE TO RELATED APPLICATION

This application is a continuation of U.S. patent application Ser. No. 16/123,614, filed Sep. 6, 2018, which is a continuation of U.S. patent application Ser. No. 14/025,708, filed Sep. 12, 2013, which claims the benefit of U.S. Provisional Application 61/780,913, filed Mar. 13, 2013, and also claims the benefit of U.S. Provisional Application 61/700,842, filed Sep. 13, 2012, all of which are incorporated herein by reference in their entireties for all purposes.

FIELD OF THE DISCLOSURE

The present disclosure relates to fluorinated polymeric emulsions, and more specifically, to tetrafluoroethylene-copolymer (TFE-copolymer) emulsions for medical applications.

BACKGROUND OF THE DISCLOSURE

Polytetrafluoroethylene (PTFE) co-polymers are well known in the art. PTFE co-polymers are of great use in many industries, but are particularly useful in medical applications due to their inertness and biocompatibility.

While useful in many respects, utilizing PTFE copolymers in solution for medical applications poses difficulties. PTFE copolymers that are water-soluble are not useful for many medical applications because they are not as inert or resistant to dissolution in an aqueous environment. On the other hand, PTFE copolymers that are insoluble in water are often very hydrophobic, which is also problematic. In particular, the solvents used to solubilize these types of tetrafluoroethylene co-polymers can be highly toxic or otherwise detrimental to living tissue. Thus, using such a solution in vivo may not be an ideal scenario.

In addition, because of the hydrophobic nature of insoluble PTFE copolymers, mixing these copolymers with a hydrophilic therapeutic agent is also difficult because the solvents suitable to dissolve PTFE copolymers are generally not suitable to dissolve hydrophilic agents. One approach for mixing a hydrophilic agent with PTFE-copolymer is to form a colloid, such as an emulsion. To be useful for a medical application, however, the drug emulsion should be relatively kinetically-stable. The very hydrophobic nature of the fluoropolymers makes forming a stable emulsion difficult without the use of a surfactant or a cosolvent to control the chemical and thermodynamic instabilities. In fact, the use of combining surfactants and fluoropolymer is the conventional way to form a PTFE emulsion. Little is known however about how to do so without a surfactant or a cosolvent, especially with cosolvents or surfactants that have a low toxic potential.

Thus, there is a need to be able to formulate polytetrafluoroethylene copolymers in less harmful solvents and/or to be able to admix hydrophilic agents with these polytetrafluoroethylene co-polymers. In particular, there is a need to be able to formulate polytetrafluoroethylene co-polymers in low toxicity solvents, such as those solvents classified by the FDA as "Solvents with Low Toxic Potential (Class III Solvents)."

Preferably, it would be desirable to be able to form kinetically stable emulsions with fluoropolymers without the addition of another component, such as a surfactant, but with the polymer material itself serving as a biocompatible surfactant for formulations comprising hydrophilic agents.

SUMMARY OF THE DISCLOSURE

The present disclosure is directed to a class of fluorinated copolymers, such as PTFE copolymers, that can be dissolved in low toxicity solvents, such as Class III Solvents, and that enable the creation of stable water-in-solvent emulsions comprising the fluorinated copolymers dissolved in a low toxicity solvent and a hydrophilic agent (e.g., a therapeutic agent) dissolved in an aqueous solvent, such as water or saline. Of particular noteworthiness is the fact that the fluorinated copolymers of the current disclosure can form kinetically stable emulsions in the absence of an additional surfactant or cosolvent. In addition, the tetrafluoroethylene-copolymer (TFE) emulsions, in accordance with this disclosure, can be homogenously mixed with hydrophilic agents such that the mixing occurs at a microscopic level (that is, the hydrophilic agent phase comprises a scale of less than about 500 nm, as measured by Raman spectroscopy), and at a molecular level (that is, the hydrophilic agent phase comprises a scale of about the size of the hydrophilic agent molecular size, as measured by modulated differential scanning calorimetry). These emulsions are useful, inter alia, for coating medical devices and living tissues, optionally with therapeutic agents, in a uniform manner and for use in filling interstitial spaces in living tissue or occluding a lumen or a complex system of lumens in a living organism, e.g., liquid embolic therapy.

One aspect of the disclosure is that the class of fluorinated co-polymers of the disclosure form kinetically stable emulsions in the absence of an additional surfactant or cosolvent to control chemical and thermodynamic instabilities. Generally, fluoropolymers fall into one of two categories: those that dissolve in non-aqueous and often toxic solvents and those that are highly water-soluble. For the non-water soluble fluoropolymers, the use of combining surfactants and fluoropolymers to form emulsions is well known. These admixtures in the form of emulsions allow for either hydrophobic or hydrophilic agents to be admixed with fluoropolymers. However, fluoropolymers comprising surfactant like properties, i.e., that have the ability to form a kinetically stable emulsion in the presence of a hydrophilic agent, are not known in the art. The ability of the fluorinated co-polymers of the disclosure to form kinetically stable emulsions for medical applications without the addition of another component, such as a surfactant or cosolvent, is unique.

One embodiment of the disclosure is directed to a class of TFE copolymers that can be dissolved in low toxicity solvents, such as Class III Solvents, and that enable the creation of stable water-in-solvent emulsions comprising the TFE-copolymers dissolved in low toxicity solvents and a hydrophilic agent (water-soluble therapeutic agent) dissolved in water. Said TFE copolymers include copolymers of TFE with functional monomers that comprise acetate, alcohol, amine or amide functional groups, as well as combinations thereof, such as poly(tetrafluoroethylene-vinyl acetate) (TFE-VAc), poly(tetrafluoroethylene-vinyl alcohol) (TFE-VOH), and poly(tetrafluoroethylene-co-vinyl alcohol-co-vinyl[aminobutyraldehyde acetal])(TFE-VOH-AcAm). Solvents comprise any non-aqueous solvent that is miscible with water, will dissolve the PTFE copolymer, and preferably exhibit low toxicity, e.g., water-miscible Class III Solvents. These emulsions are useful, inter alia, for coating medical devices and living tissue, optionally with therapeutic agents, in a uniform manner and for use in filling an empty space or gap in a living tissue or occluding a lumen or a complex system of lumens in living tissue, e.g., liquid embolic therapy.

Other embodiments described herein include methods of making and using said emulsion, along with devices, systems, and methods utilizing additional devices utilized in the delivery or application of the described emulsion.

BRIEF DESCRIPTION OF THE DRAWINGS

The accompanying drawings are included to provide a further understanding of the disclosure, and are incorporated in and constitute a part of this specification, illustrate embodiments of the disclosure, and together with the description, serve to explain the principles of the disclosure.

FIGS. 4(a) through 4(d) are overhead views of storage vessels for (a) Suspension D, (b) Suspension V, (c) Kinetically Unstable Emulsion D, (d) Kinetically Stable Emulsion V, as described in the Examples.

FIGS. 5(a)(i) through 5(d)(i) are side views of the storage vessels for (a) Suspension D, (b) Suspension V, (c) Kinetically Unstable Emulsion D, (d) Kinetically Stable Emulsion V, as described in the Examples.

FIGS. 5(a)(ii) through 5(d)(ii) are schematic representations of the physical state of the emulsions in the storage vessels of FIGS. 5(a)(i) through 5(d)(i), respectively.

FIGS. 9(a) and 9(b) depict a porcine kidney pre- and post-embolization, respectively.

DETAILED DESCRIPTION OF THE ILLUSTRATED EMBODIMENTS

Figure 1:
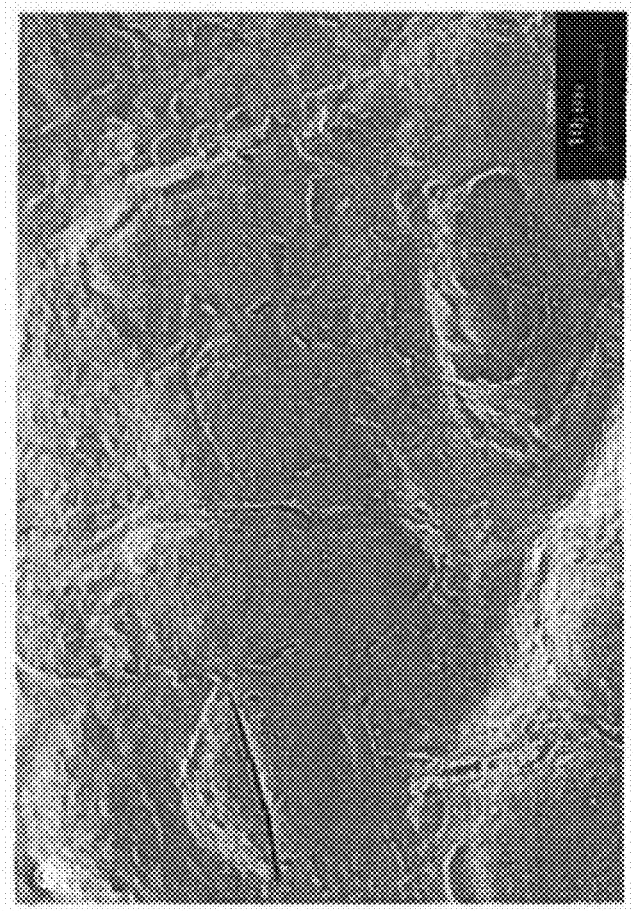
FIG. 1 depicts an SEM image of a tetrafluoroethylene copolymer emulsion embodiment comprising a therapeutic agent uniformly distributed therein.

Persons skilled in the art will readily appreciate that various aspects of the present disclosure can be realized by any number of methods and apparatuses capable of performing the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

Although the present disclosure can be described in connection with various principles and beliefs, the present disclosure should not be bound by theory. For example, the present disclosure is described herein in connection with stable fluoropolymer emulsions in the medical context. However, the present disclosure can be applied toward any context wherein a fluoropolymer emulsion has utility.

In addition, all published documents, including all US patent documents, mentioned anywhere in this application are hereby expressly incorporated by reference in their entirety.

The present disclosure is directed to a class of fluorinated copolymers that can be dissolved in non-aqueous solvents, that have low toxicity to living cells, and that enable the creation of kinetically stable water-in-solvent emulsions. The present disclosure also comprises water-in-solvent kinetically stable emulsions of a PTFE copolymer dissolved in a non-aqueous solvent and a hydrophilic agent (water-soluble agent) dissolved in water. These emulsions are useful for, inter alia, coating medical devices and living cells, tissues, or organs, for coating substrates with a fluoropolymer and therapeutic agent mixture in a substantially uniform manner, for filling an empty space or gap surrounding by living tissue or occluding a lumen in a living organism, e.g., embolotherapy, and for use in tissue bulking applications.

Embolotherapy is a minimally invasive procedure performed to treat a variety of vascular pathologies, including, but not limited, to preoperative management of hypervascularized tumors and arteriovenous malformations. Embolotherapy involves the intentional blockage or embolization of a cavity, blood vessel, or a system of blood vessels with an object to control or prevent blood flow to a vascular pathology, e.g., hypervascularized tumors and arteriovenous malformations. Hypervascularized tumors have abnormally large numbers of blood vessels providing circulation and are either malignant or benign. Arteriovenous malformations are abnormal connections between arteries and veins whose presence can lead to stroke and death. Hypervascularized tumors and arteriovenous malformations can occur in many areas of the body. In addition, embolization can be used for treating fistulae, endoleaks, aneurysms (by filling or plugging the aneurismal sac), and embolizing a vessel to control bleeding due to lesions (e.g. organ bleeding, gastrointestinal bleeding, vascular bleeding, as well as bleeding associated with an aneurysm), for access closure, and for chronic total occlusion. Embolic agents are generally delivered to a designated area of the body through a catheter device. The embolic agents can be permanent implants, biodegradable implants, or temporary implants removed by a second procedure. Embolic agents can be delivered in a solid form (such as a balloon on a catheter, or metal coils) or as a liquid form that hardens in vivo into a second form that can be a solid, a gel, or an intermediate state. In the case of polymer-based liquid embolics, upon injection of the embolic solution to a treatment site, during the hardening process, the "liquid phase", i.e. the solvent, of the embolic diffuses away from the site, leaving behind a precipitated polymer that obstructs blood flow to the pathology.

Usually, polymer based liquid embolic compositions comprising a water insoluble polymer dissolved in a solvent, such as lipiodol, are delivered to a target site using syringe or catheter techniques. Upon contact with blood or other bodily fluids, in a process referred to herein as hardening, the solvent dissipates and the water insoluble polymer precipitates at the site, undergoing a transition from a liquid state to a solid state or a gel state or an intermediate state, as a congealed mass or as multiple discrete particles, thereby embolizing the site.

There are examples of such polymer-based liquid embolic compositions in the art. These known compositions include poly (ethylene-vinyl alcohol) dissolved in dimethylsulfoxide (DMSO), poly (hydroxyethyl methacrylate) dissolved in ethanol (EtOH), cyanoacrylate dissolved in lipiodol, and poly (lactide-glycolide) dissolved in N-methylpyrrolidone (NMP). DMSO, EtOH, lipiodol, and NMP have well known toxicities and side effects such as vasospasm, sclerosis, intoxication, and pain. Thus, their use must be carefully monitored when injected into a blood vessel, an organ, or other target site. In addition, these solvents release noisome vapors that can cause great discomfort for the patient and the surgical and medical staff. DMSO and NMP can also dissolve and damage common catheter and interventional materials, so these solvents require special and/or expensive catheters and other surgical equipment.

Thus, one embodiment of the disclosure is directed to a class of fluorinated copolymers, such as TFE copolymers, that can be dissolved in non-aqueous solvents that are of low toxicity to living tissue and that enable formation of kinetically stable water-in-solvent emulsions. In addition, said water-in-solvent emulsions do not require specialized catheters because the described emulsions do not or only inconsequentially damage commonly used catheters. Another embodiment of the disclosure is directed to a class of fluorinated copolymers that can be dissolved in non-aqueous solvents that are of higher toxicity to living tissue, such as dimethylsulfoxide (DMSO) or methylpyrrolidone (NMP), and that enable formation of kinetically stable water-in-solvent emulsions, whereby the toxicity of the solvent is reduced by dilution from the emulsion. Another embodiment of the disclosure is directed to a class of fluorinated copolymers that can be dissolved in non-aqueous solvents that can damage common catheter materials, such as DMSO or NMP, and that enable formation of kinetically stable water-in-solvent emulsions, whereby the damage potential of the solvent is reduced or eliminated by dilution from the emulsion. The present disclosure also comprises water-in-solvent kinetically stable emulsions of a fluorinated copolymer dissolved in a non-aqueous solvent and a hydrophilic agent (water-soluble agent) dissolved in water.

As the examples below depict, fluorinated copolymers, such as poly(tetrafluoroethylene-vinyl acetate) (TFE-VAc) and poly(tetrafluoroethylene-vinyl alcohol) (TFE-VOH), can be soluble in solvents and cosolvents with reduced toxicity, side effects, and volatility, and that do not damage commonly used catheters. These solvents and cosolvents include, but are not limited to alkylene glycol (including propylene glycol, oligoethylene glycol, and oligopropylene glycol), aqueous alkylene glycol, polar aprotic solvents such as DMSO, NMP, and combinations thereof. Propylene glycol, oligoethylene glycol, and their aqueous cosolvents, in particular, are known for their extremely low toxicity, widespread intravenous pharmaceutical utility, and are classified as Generally Recognized as Safe (GRAS). They are used as drug carriers for the treatment of vasospasm and pain.

TFE-VOH and TFE-VAc with a TFE mole content as low as 15.5% are insoluble in water. Surprisingly, however, as shown in the Examples below, TFE-VAc and TFE-VOH are soluble in alkylene glycol and aqueous alkylene glycol with 40% water (w/w) at physiological temperatures. These cosolvent systems are able to solubilize hydrophilic contrast agents, therapeutic compounds, and other water-soluble agents. When dissolved in alkylene glycol or aqueous alkylene glycol, or in aqueous DMSO or in aqueous NMP at 40% (w/w) water, these fluorinated TFE copolymers precipitate upon contact with blood or saline and harden to form solid or gel-like embolic masses, as a congealed mass or as multiple, discrete particles.

In contrast, vinyl alcohol copolymers made from the hydrocarbon analogue to TFE, namely poly(ethylene-vinyl alcohol) (EVOH), at an ethylene mole content as low as 15.5% are water-soluble. When dissolved in organic solvents, these low ethylene-containing copolymers will not precipitate upon contact with blood or saline and will not harden to form an embolic mass. Furthermore, the art teaches such EVOH compounds are soluble in solvents such as alkylene glycol only at temperatures significantly higher than physiological temperature. One of ordinary skill in the art would not expect a more hydrophobic polymer like TFE-VOH to be soluble in alkylene glycol and aqueous alkylene glycol at physiological temperatures.

The fact that TFE-VAc and TFE-VOH have solvent behaviors as described above is surprising and unexpected, especially when compared to similar copolymers in the art, such as EVOH or such as poly(ethylene-vinyl acetate). Consequently, since TFE-VAc and TFE-VOH can be dissolved in high water content, cosolvent systems, the challenges associated with solvent toxicity/side effects, solvent vapor volatility, and solvent incompatibility with catheters are greatly reduced. Furthermore, these systems have viscosities that allow for needle, catheter, and microcatheter delivery. Thus, due to their low viscosity and low toxicity, these TFE-VAc and TFE-VOH embolic compositions can be delivered to anatomical target sites with fewer complications than current embolic therapies. These materials also have wide-ranging application as medical coating agents or tissue bulking and/or occluding agents, alone, or in combination with various occlusive casings of any desired shape.

Another embodiment of the disclosure comprises a water-in-solvent kinetically stable emulsion of said fluorinated copolymer dissolved in a non-aqueous solvent and a hydrophilic agent, such as a drug, dissolved in water. These compositions can be used in embolic therapy while also delivering, for example, a hydrophilic drug and/or a contrast agent.

The present disclosure also comprises said water-in-solvent kinetically stable emulsions of said fluorinated copolymer dissolved in a non-aqueous solvent and a hydrophobic drug complexed with an inclusion complex and dissolved in water to create a substantially uniform coating on substrates, including medical devices and living tissue, or a polymeric mass. Alternatively or in addition thereto, a drug can be dissolved in said non-aqueous solvent or conjugated with the copolymer, and in either case, are then emulsified according to the present disclosure.

Substrates, such as medical devices or a tissue, are commonly coated with a drug-polymer matrix by dissolving an agent, such as a drug, and the polymer in a solvent and applying this solution to the substrate. However, hydrophilic agents (such as proteins, peptides, contrast agents, hydrophilic drugs, pharmaceutical salts, and steroid derivatives, and/or other agents described below) are often soluble only in water, while many biocompatible polymers are soluble only in organic solvents. To circumvent this solubility problem, the hydrophilic agent can be suspended in a non-aqueous polymer solution. The resulting suspension can then be applied to a substrate. However, the hydrophilic agent can readily precipitate from these suspensions, thereby obstructing the spray nozzles of coating equipment, or thereby settling out of dipping baths, thereby decreasing coating efficiency and resulting in poor coating uniformity (as shown in Examples 2 and 3). Furthermore, the potency of hydrophilic agents can be compromised by suspension in neat organic solvents.

Several methods in the art attempt to circumvent these problems. These methods include using two separate applicators to apply separately the polymer and drug to the substrate. In this case, at least two spray nozzles are used to coat a substrate. One nozzle sprays an organic solution of the polymer, and the other nozzle sprays an aqueous solution of the hydrophilic agent (see e.g. U.S. Pat. No. 5,980,097). An alternate method involves creating a suspension of the hydrophilic drug in the organic polymer phase and agitating the suspension to keep it "well mixed". The above-mentioned methods require expensive equipment, are unreliable (e.g. spray nozzles can become clogged or dipping baths settle out), and/or are time consuming. Further, the distribution of the hydrophilic agent is not uniform and the potency of the hydrophilic agent may still be compromised.

Fluorinated copolymers are particularly useful in these medical coatings due to their biocompatibility, durability, and inertness. Such fluorinated copolymers with these preferred chemical and physical properties are often water insoluble. Thus, a common solvent cannot be used to solubilize both a hydrophilic drug and the hydrophobic fluoropolymer.

Compositions comprising an emulsion of a hydrophobic fluorinated copolymer and a hydrophilic agent, that is kinetically stable, that protects the agent against damage from exposure to the solvent, and that can be conveniently applied to a substrate would be of great utility, particularly if the solvent is biocompatible and safe for use in humans. As stated above, the novel water-in-solvent, kinetically stable emulsions comprising a fluorinated TFE copolymer dissolved in a non-aqueous solvent and a hydrophilic agent dissolved in water will alleviate the problem of uneven distribution of said hydrophilic agent and/or clogging of spray nozzles and/or settling of dipping baths and/or the need to have special equipment to coat evenly a substrate. Advantages can also be realized with the novel water-in-solvent kinetically stable emulsions comprising a fluorinated TFE copolymer dissolved in a non-aqueous solvent and a therapeutic agent dissolved in said non-aqueous solvent.

As defined herein, "solvent" is an organic solvent that is capable of dissolving the fluoropolymer copolymer with out the addition of any other agent; the solvent is water-miscible, and preferably, exhibits low toxicity. As defined herein "low toxicity solvents" include "Class III Solvents" as defined by the U.S. Food and Drug Administration (FDA) or the International Conference on Harmonixation of Technical Requirements for Registration of Pharmaceuticals for Human Use (ICH) such as acetone and dimethyl sulfoxide and solvents "Generally Recognized as Safe" (GRAS) as defined by the FDA such as propylene glycol (See Guidance for Industry: Q3C: "Tables and List", FDA Guidance, Rev 1, November 2003 and "ICH Guideline: Harmonization of Residual Solvents in Pharmaceuticals", LS Wigman, Pharm Tech, p 102-108, October 1996, both of which are hereby incorporated by reference in their entirety.) In addition, a solvent can also comprise any water miscible solvent with relatively low toxicity, e.g., some that are FDA and/or ICH classified Class 2 solvents with water miscibility and relatively low toxicity, such as acetonitrile, dioxane, formamide, dimethylformamide, pyridine, NMP, methylpyrrolidone, dimethylacetamide, ethylene glycol, methyoxymethanol, pyridine, piperidine, sulfolane, tetrahydrofuran, trichloroacetic acid, and the like. Other suitable low toxicity solvents include oligoethylene glycol such as polyethylene glycol and polyethylene oxide. Table 1 (adopted from the FDA Guidance document "Class III Solvents") comprises a list of Class III Solvents.

TABLE 1

FDA Class III Solvents

| | |
|---|---|
| Acetic Acid | Isopropyl acetate |
| Acetone | Methyl acetate |
| 1-Butanol | 3-Methyl-1-butanol |
| 2-Butanol | Methylethyl ketone |
| Butyl acetate | Methylisobutyl ketone |
| Dimethyl sulfoxide | 2-Methyl-1-propanol |
| Ethanol | 1-Pentanol |
| Ethyl acetate | 1-Propanol |
| Ethyl formate | 2-Propanol |
| Formic Acid | Propyl acetate |
| Isobutyl acetate | Methyl acetate |

As used herein, a "substrate" is any surface which can be coated or imbibed with an emulsion embodiment of the current invention and includes the surfaces of medical devices, films, membranes, and other objects having a surface. A substrate can also include a living surface such as the intima or adventitia of a vessel; the inner or outer lining of an organ such as the esophagus, stomach, liver, intestine, etc.; a vertebra; a sinus; a sulcus; a tissue such as a dermal tissue, muscular tissue, pericardial tissue, or any other biological tissues or organs.

As used herein a "colloid" is a substance microscopically or nanoscopically dispersed evenly throughout another substance. As used herein, an "emulsion" is a suspension of a first liquid in a second liquid. As defined, the first liquid would be discontinuous, and the second liquid would be continuous. Stated differently, the first liquid would comprise discrete micelles or microphases or nanophases suspended in the second liquid. The nanophase size may be as small as the order of the scale of the substance molecular size. A water-in-solvent emulsion comprises water as the first liquid and a solvent as the second liquid. In accordance with the present disclosure, each liquid can contain one or more compounds that are soluble in one liquid but not the other.

As used herein, "opacity point" means the point at which an emulsion becomes opaque during the drop wise addition of water. This amount of water is determined to be the maximum water content that the kinetically stable copolymer emulsion can tolerate without kinetic instability, and is termed the opacity point. This definition is demonstrated in Example 11 and contained within the example.

As used herein, "kinetically stable" is a degree of stability wherein a component of an emulsion remains suspended, (i.e., precipitation, flocculation, sedimentation, separation, or coalescence of a component is not visibly detectable with the naked eye) for at least one minute, at least 5 minutes, at least 30 minutes, at least 60 minutes, at least one month, at least 4 months, or at least one year. Alternatively, as used herein "kinetically stable" is a degree of stability wherein the dispersed component of an emulsion remains sufficiently suspended to uniformly coat a substrate without a third emulsifying agent such as a surfactant, solvent, cosolvent, or the like and without the need for continuous stirring or agitation or complex mixing systems. As used herein, an "unstable emulsion" is an emulsion that is not kinetically stable.

As used herein, a "uniform coating," means the components that make up the coating have a substantially even distribution. FIG. 1 depicts a uniform coating of an emulsion as described herein.

As used herein, "water miscible" means the property of said solvent to mix in all proportions with water, to form a homogeneous solution.

As used herein "water soluble agent" or hydrophilic agent means an agent that dissolves in water and can include a hydrophilic therapeutic agent, protein, peptide, contrast agent, pharmaceutical, or drug, or a inclusion agent (e.g., cyclodextrin) complexed with a hydrophobic therapeutic agent, contrast agent, pharmaceutical, or drug (e.g., paclitaxel or dexamethasone). An inclusion agent, as used herein, is an amphiphillic substance that comprises both hydrophilic and hydrophobic moieties and is capable of sequestering or shielding a hydrophobic agent from a hydrophilic (aqueous) environment. A hydrophobic agent means an agent that is not a water soluble agent and can include a hydrophobic therapeutic agent, protein, peptide, contrast agent, pharmaceutical, or drug, or a inclusion agent.

As used herein, "evaporation" means the passive or active removal of a first substance, such as a solvent or solvent mixture, from a second substance, such as a second solvent mixture, a solid, or another substance. Evaporation can comprise air-drying, flash-drying, freeze-drying, or any other technique that enables the evaporation of a solvent. Such techniques result in the formation of a dry coating.

As used herein, "medical device" includes vascular graft, stent, stent graft, medical balloons (e.g., angioplasty balloon), embolic filter, catheter, heart valve, heart valve frame or pre-stent, occluder, sensor, marker, closure device, filter, embolic protection device, anchor, an implantable pacing lead, neurostimulation lead, and gastrointestinal sleeves.

As used herein, a "therapeutic agent," (also referred to as "beneficial agent," or "drug") refers to any substance that aids in any procedure, e.g., diagnostic, surgical, interventional, or therapeutic procedures, or that aids in providing a diagnostic, surgical, interventional, therapeutic and/or curative effect. A therapeutic agent can be hydrophilic, hydrophobic, or amphiphillic.

More specifically, "therapeutic agents" include, but are not limited to, contrast agents such as iohexol, iopamidol iopromide, gold nanoparticles, or the like; proteins and peptides such as monoclonal antibodies capable of blocking smooth muscle cell proliferation, inhibitory antibodies, antibodies directed against growth factors, and thymidine kinase inhibitors; anti-coagulants such as D-Phe-Pro-Arg, chloromethyl ketone, an RGD peptide-containing compound, heparin, hirudin, antithrombin compounds, platelet receptor antagonists, anti-thrombin antibodies, antiplatelet receptor antibodies, prostaglandin inhibitors, platelet inhibitors, antiplatelet peptides, growth factors, such as vascular cell growth promoters such as growth factors, transcriptional activators, translational promotors; vascular cell growth inhibitors such as growth factor inhibitors, growth factor receptor antagonists, transcriptional repressors, translational repressors, replication inhibitors, bi-functional molecules consisting of a growth factor and a cytotoxin, bifunctional molecules consisting of an antibody and a cytotoxin; protein kinase and tyrosine kinase inhibitors (e.g., tyrphostins, genistein, quinoxalines), prostacyclin analogs, cholesterol-lowering agents, statins, angiopoietins, agents that interfere with endogenous vasoactive mechanisms, inhibitors of leukocyte recruitment such as monoclonal antibodies, cytokines, hormones such as β-estradiol 3-(β-D-glucuronide) sodium salt, β-estradiol 3-sulfate sodium salt, -β-estradiol 17-(β-D-glucuronide) sodium salt, estrone 3-sulfate sodium salt, estrone 3-sulfate potassium salt, estradiol acetate, estradiol cypionate; anesthetics such as lidocaine and ketamine salt; analgesics such as acetylsalicylic acid, α-methyl-4-(isobutyl)phenylacetic acid, diclofenac sodium salt, beta hydroxy acids, salicylic acid, sodium salicylate, naproxen sodium, antibiotics; anti-inflammatory agents such as dexamethasone, dexamethasone sodium phosphate, dexamethasone sodium acetate, estradiol, prednisolone, corticosterone, budesonide, estrogen, sulfasalazine and mesalamine, sirolimus and everolimus (and related analogs), and combination thereof; and also include cells, mammalian cells, eukaryotes, prokaryotes, somatic cells, germ cells, erythrocytes, platelets, viruses, prions, DNA, RNA, vectors, cellular fractions, mitochondria, and the like; anti-neoplastic/antiproliferative/anti-mitotic agents such as paclitaxel, dicumarol, and analogues thereof, rapamycin and analogues thereof, beta-lapachone and analogues thereof, 5-fluorouracil, cisplatin, vinblastine, vincristine, epothilones, endostatin, angiostatin, angiopeptin, and combinations thereof; anesthetic agents such as aspirin, lidocaine, bupivacaine and ropivacaine, prostaglandin inhibitors, platelet inhibitors, cytotoxic agents such as docetaxel, doxorubicin, paclitaxel, and fluorouracil and analogues thereof, cytostatic agents, cell proliferation affectors, vasodilating agents, cilostazol, carvedilol, antibiotics, sclerosing agent such as ethanol and combinations thereof.

The classes of fluorinated copolymers that can be dissolved in non-toxic, non-aqueous solvents and that can form water-in-solvent stable emulsions include PTFE copolymers that comprise at least about 77 mole % of organic functional groups comprising acetate, alcohol, amine, or amide, or combinations thereof, and at least about 15 mole % of TFE. In another embodiment, the water-in-solvent stable emulsion comprises a water-miscible organic solvent and can tolerate at least about 50%, about 47%, about 40%, about 35%, about 30%, about 27%, about 25%, about 23%, about 22%, or a mass range thereof, of water. In addition, the water-in-solvent emulsion can comprise up to 1%, up to 5%, up to 10%, or any other percentage by weight of said fluorinated copolymers that is suitable based on the particular copolymer selected, and can further comprise up to 0.1%, up to 0.5%, up to 1%, up to 5%, up to 10%, up to 15%, up to 25%, up to 35%, up to 45%, or any other percentage by weight of said fluorinated copolymers that is suitable, dependent on the particular water soluble agent selected.

Methods of making fluorinated copolymers of the disclosure are described below and are known in the art (see e.g., Modena et al., "Vinyl Acetate and Vinyl Alcohol Copolymers with Tetrafluoroethylene," European Polymer Journal, 1967, v. 3, pp. 5-12). The fluorinated copolymers of the disclosure can have the characteristics listed on Table 2.

TABLE 2

Monomer Ratios

| Fluorinated copolymers | General Formula | Ratio Range of n | Ratio Range of m |
|---|---|---|---|
| TFE-VOH | $[TFE]_n$-$[VOH]_m$ | 15.5-23.5 | 76.5-84.5 |
| TFE-VAc | $[TFE]_n$-$[VAc]_m$ | 15.5-23.5 | 76.5-84.5 |
| TFE-Amine | $[TFE]_n$-$[Amine]_m$ | 15.5-23.5 | 76.5-84.5 |
| TFE-Amide | $[TFE]_n$-$[Amide]_m$ | 15.5-23.5 | 76.5-84.5 |

As demonstrated in the Examples below, the emulsions of the disclosure can be used to uniformly coat medical devices with the model hydrophilic agent dexamethasone sodium phosphate (DSP). In this embodiment, a kinetically stable emulsion can be formed by combining a TFE-VAc/acetone solution and a DSP/water solution. The resulting kinetically stable emulsion was used to spray coat a film substrate. Upon solvent evaporation of the acetone and water, this method produced a uniform coating with high drug load (69% DSP by mass). In fact, the final coating composition (69% drug, 31% polymer by mass) approximates the initial ratio of drug (73%) to total solids (by mass), indicating the uniformity of this coating method.

One embodiment of the disclosure comprises a water-in-solvent emulsion comprising a fluorinated co-polymer dissolved in a water miscible organic solvent; and a water-soluble agent dissolved in water, wherein the emulsion is kinetically stable. Another embodiment of the disclosure comprises a water-in-solvent emulsion comprising a fluorinated co-polymer dissolved in a water miscible organic solvent; and a water-soluble agent dissolved in water, wherein the opacity point for the system is greater than 5% water and less than 60% by weight. In various embodiments, said copolymer comprises tetrafluoroethylene. In addition, the second monomer of said copolymer can comprise an organic functional group selected from the group consisting of acetate, alcohol, amine, and amide functional groups, and combinations thereof. In another embodiment, said fluorinated copolymer is TFE-VAc. In another embodiment, said fluorinated copolymer is TFE-VOH. In various embodiments, said water-soluble agent is a therapeutic agent, pharmaceutical, or drug. In another embodiment, said water-soluble agent is a contrast agent. In another embodiment, said therapeutic agent is hydrophobic. In another embodiment, said water-soluble agent is an inclusion complex consisting of a hydrophilic complexing agent and a hydrophobic therapeutic agent, pharmaceutical, or drug. In another embodiment, the inclusion complex consists of a cyclodextrin molecule and a hydrophobic therapeutic agent. In another embodiment, said water-in-solvent emulsion is applied onto a substrate using a single applicator. In another embodiment, the applicator is a single spray nozzle. In another embodiment, said substrate is selected from the group consisting of a medical device, a living organ, and a living tissue. In another embodiment, said substrate is a medical device. In another embodiment, said medical device is selected from the group consisting of a vascular graft, stent, stent graft, vascular patch, soft tissue patch, heart valve, angioplasty balloon, embolic filter, catheter, suture, and an implantable pacing lead. In another embodiment, said emulsion remains kinetically stable, requiring neither mixing nor agitation during application onto said substrate. In another embodiment, said water-in-solvent emulsion is applied to a substrate and the water miscible organic solvent and water are removed (through evaporation or drying) leaving a dry coating comprising the fluorinated copolymer and a therapeutic agent on the substrate. In another embodiment, said water-in-solvent emulsion is applied to a substrate and the water miscible organic solvent is removed (through extraction or leaching) to harden the emulsion, leaving a hydrated coating comprising the fluorinated copolymer and a therapeutic agent on the substrate. In another embodiment, said water-in-solvent emulsion is applied to a substrate, the water miscible organic solvent and water are removed (through evaporation or drying), leaving a dry coating comprising the fluorinated copolymer, and a therapeutic agent evenly distributed on said substrate. In another embodiment, said water miscible organic solvent is selected from the group shown in Table 1. In another embodiment, said water miscible organic solvent is selected from the group consisting of alcohols, esters, ketones, glycols, and aldehydes, and polar aprotic solvents such as acetonitrile, dimethylformamide, dimethylsulfoxide, methylpyrrolidone, and the like.

Another embodiment of the disclosure comprises a coating for a substrate, e.g., a medical device or a tissue, comprising a fluorinated copolymer, a solvent phase comprising a water miscible organic solvent, a water-soluble agent, and a water phase; wherein when said components are mixed, they form an emulsion that is kinetically stable. In another embodiment, said coating for a medical device comprises a fluorinated copolymer, a solvent phase comprising a water miscible organic solvent, a therapeutic agent, and a water phase; wherein when said components are mixed, they form an emulsion that is kinetically stable. In various embodiments, said copolymer comprises tetrafluoroethylene. In addition, the second monomer can comprise functional groups selected from the group consisting of acetate, alcohol, amine, and amide, and combinations thereof. In another embodiment, said fluorinated copolymer is TFE-VAc. In another embodiment, said fluorinated copolymer is TFE-VOH. In another embodiment, said water-soluble agent is a therapeutic agent, pharmaceutical, or drug. In another embodiment, said emulsion is capable of being applied onto a medical substrate using a single applicator. In another embodiment, said emulsion is capable of being applied onto a medical device using a single applicator. In another embodiment, said single applicator is a single spray nozzle (or other applicator system such as a needle, catheter, syringe, dispensing tip, pipet, etc.). In another embodiment, said emulsion remains kinetically stable, requiring neither mixing nor agitation during application onto said substrate. In another embodiment, said water-in-solvent emulsion is applied to a substrate, and the water miscible organic solvent and water are removed (through evaporation or drying) leaving a dry coating comprising the fluorinated copolymer and a water-soluble agent on the substrate. In another embodiment, said water-in-solvent emulsion is applied to a substrate and the water miscible organic solvent and water are removed (through evaporation or drying) leaving a dry coating comprising the fluorinated copolymer and a water-soluble agent distributed evenly on said substrate. In another embodiment, said water-in-solvent emulsion is applied to a substrate, and the water miscible organic solvent is removed (through partial evaporation, extraction, or leaching) to harden the emulsion leaving a hydrated coating comprising the fluorinated copolymer and a water-soluble agent on the substrate. In another embodiment, said fluorinated copolymer and a water-soluble agent are evenly distributed on said medical device. In another embodiment, said medical device is selected from the group consisting of a vascular graft, stent, stent graft, vascular patch, soft tissue patch, heart valve, suture, angioplasty balloon, embolic filter, catheter, and an implantable pacing lead. In another embodiment, said water miscible organic solvent is selected from the group shown in Table 1 (supra). In another embodiment, said water miscible organic solvent is selected from the group consisting of alcohols, esters, ketones, glycols, and aldehydes, and polar aprotic solvents. In various embodiments, the coating can be phase mixed on the microscopic scale, that is, the mixed phase domains comprise a scale of less than about 500 nm, as measured by Raman spectroscopy. In various embodiments, the coating can be phase mixed on the molecular level, that is, the mixed phase domains comprise a scale of about the size of the therapeutic agent molecular size, as measured by modulated differential scanning calorimetry (M-DSC). In such molecularly phase mixed coatings, the coating can have at least a 50% reduction or at least an 80% reduction in its excess heat capacity on a tetrafluoroethylene copolymer mass basis as compared with a coating of tetrafluoroethylelne copolymer with no therapeutic agent. In various embodiments, the coating shows essentially no reversing exotherms and essentially no non-reversing exotherms on a tetrafluoroethylene copolymer mass basis in a first or second heating run using M-DSC.

Coating a substrate, e.g., a medical device or a tissue, can be used for any number of applications. Coating a substrate can occur external to the body or can occur in vivo.

In an embodiment, a method of application can comprise providing a temporary patch or cover for a tissue to serve as a protective barrier, shielding the tissue from the surrounding environment. The described emulsion can be applied to a tissue that is injured, e.g., burned, cut, inflamed, infected, traumatized, diseased, or the like. Coating a tissue can cover a large or small area. For example, the described emulsion could be applied to an area of the colon after removal of a polyp or a length of the GI tract, to act as a temporary barrier to protect the area or section from contamination or irritation from intestinal contents.

In other embodiments, an application can comprise constructing a graft in vivo. A graft can comprise for example, a vascular graft or a gastrointestinal graft. Assembling a graft in vivo can facilitate a lower delivery profile. An embodiment can comprise delivering a described emulsion and forming the emulsion into a tubular or other cannulated form in vivo. The tubular form can comprise a graft, e.g., a vascular graft or a gastrointestinal graft. An embodiment can further comprise applying a reinforcing member(s) to the formed emulsion or delivering the reinforcing members therewith to provide structural support to the assembled construct.

Similarly, another application can comprise repairing a hole or other type of structural defect within a structural member, e.g., a medical device comprising a vascular graft, in vivo. The described emulsion can be applied to the defect and will eventually harden. The terms "harden", "hardening", and the like, as used herein refer to the solvent phase diffusing out of the extruded emulsion and/or non-solvent, such as water, aqueous solvents, saline, bodily fluids such as blood and sera, infusing into the extruded emulsion. In various embodiments, a perfusion balloon can perfuse the emulsion to the graft. The balloon can remain inflated for the time required to allow for the hardening of the TFE copolymer. In other embodiments, an emulsion can be delivered through a tubular member. The distal end of the tubular member can be adapted to curve radially outward from its delivery path so that the emulsion can be released from its distal end onto the defect or application site. In order to shorten the time for hardening, an auxiliary lumen can spray a non-solvent, such as a saline solution, onto the application site during or subsequent to the application of the emulsion. For certain applications, prior to the delivery of the emulsion, emboli prevention and/or emboli capture techniques known in the art can be appropriately positioned to prevent potential undesired release of precipitated TFE copolymer particles.

In other embodiments, a described emulsion can be used to coat or apply onto one face of a tissue, organ, film or sheet of material or a portion thereof, such as a graft. The applied emulsion can function as an adhesive. For example, an emulsion can be used to adhere a graft to a substrate such as a tissue or a medical device In another embodiment, a device can comprise at least two layers having a described emulsion there between. The at least two layers can be a film or sheet. The emulsion located in between the layers can facilitate sealing a layer if it has been punctured, eroded, torn, or otherwise damaged. The device can be a graft member. In other embodiments, the device can be a septum. Similarly, said emulsion can be useful as a leakstop or sealant type material.

Filling gaps or void spaces can have many applications. Filling gaps or void spaces can occur external to the body or in vivo. In an embodiment, the described emulsion can facilitate treatment of an endoleak or to facilitate sealing or adhering at least a portion of the outer surface of a graft, stent, or stent graft to the surrounding vessel or a neighboring graft, stent, or stent graft. For example, with reference to FIGS. 11a to 11f, a delivery system 1100 can comprise an emulsion delivery catheter 1110, that is an emulsion source, e.g., a pre-loaded syringe. In various embodiments, the emulsion delivery catheter 1110 is adapted so that it can access the endoleak. For example, the delivery catheter 1110 can be steerable and/or have a curved or angled distal region. The described emulsion 1130 can be transportable via a lumen of the emulsion delivery catheter. In various embodiments, the emulsion 1130 is able to flow through a 2.5 Fr catheter up to 12 Fr catheter.

Optionally, system 1100 can further comprise a positionable backstop or containment mechanism, such as catheter 1120, passable through a lumen of catheter 1120 and having an expandable member 1125 that can serve as a temporary backstop to contain the injected emulsion 1130 and remain in place to the extent necessary for hardening. In various embodiments, a containment mechanism can comprise a distensible sleeve as shown in FIG. 3. In various embodiments, a backstop mechanism can be as shown in FIGS. 11a to 11f, a catheter 1120 comprising an expandable member 1125, such as a balloon, on a distal section. The expandable member 1125 can be adaptable to different cross-sectional areas to create a sufficiently sealed backstop, e.g., a compliant balloon. The catheter 1120 and/or expandable member 1125 can be adapted to have a lubricious or non-stick surface so that it can be withdrawn through the emulsion 1130 after the emulsion 1130 is sufficiently hardened. In various embodiments, the emulsion 1130 can be adapted to be radio-opaque, temporarily or permanently.

A method of treating an endoleak can comprise positioning delivery catheter 1110 into an interstitial space 1150 between an endoprosthesis and a vessel or between two adjacent endoprostheses as shown in FIGS. 11a through 11f. The emulsion 1130 can be transported through the lumen of the catheter 1110 to form a seal 1135. Optionally, prior to delivering the emulsion 1130, a backstop mechanism can be set into position, if appropriate. For example, a compliant balloon 1125 can be inflated at a desired location within the interstitial space 1150 to keep the emulsion 1130 contained within the desired amount of space 1150 to be filled.

Alternatively, the entire aneurismal sac can be filled. After a predetermined dwell time sufficient for the emulsion 1130 to sufficiently harden, which can be dependent on the location or volume of emulsion 1130 injected, the expandable member 1125 can be withdrawn.

Described emulsions can be combined with other materials for alternate properties or morphologies and be used for coating or filling an interstitial space. For example, described emulsions can be mixed with a bioabsorbable material. As bioabsorption occurs, voids can form in the hardened emulsion creating a porous or sponge-like polymeric material. In various embodiments, the void spaces can be sites where tissue ingrowth can occur. Examples of bioabsorbable material includes poly(lactic acid-co-glycolic acid) (PLA-PGA) adjusted in the desired ratio to achieve the desired rate of biological absorption. Other potentially useful bioabsorbable materials include polyglycolic acid (PGA), poly-L-lactic acid (PLA), polydiaoxanone (PDS), polyhydroxybutyrate, copolymers of hydroxybutyrate and hydroxyvalerate, copolymers of lactic acid and E-caprolactone, oxidized regenerated cellulose and various forms of collagen. A preferred material is poly(glycolide-co-trimethylene carbonate) tri-block copolymer (PGA:TMC), e.g., the non-woven, bioabsorbable web material described in U.S. Pat. No. 7,659,219 by Biran et al. entitled "Highly porous self-cohered web materials having hemostatic properties," which is hereby incorporated by reference in its entirety. The proportions of this or any other selected copolymer or blends of polymers can be adjusted to achieve the desired absorption rate. Other potentially useful bioabsorbable materials including porous forms are described by U.S. Pat. No. 4,243,775 to Rosencraft et al.; U.S. Pat. No. 4,300,565 to Rosencraft et al.; U.S. Pat. No. 5,080,665 Jarrett et al.; U.S. Pat. No. 5,502,092 Barrows et al.; U.S. Pat. No. 5,514,181 to Light et al. and U.S. Pat. No. 5,559,621 to Minato et al., and published PCT application WO 90/00060 to Chu et al., all of which are hereby incorporated by reference in their entireties.

In another embodiment, the described emulsion can be mixed with a gas-producing agent that produces gas during or after the drying or hardening of the TFE copolymer emulsion to form a sponge-like material. In an embodiment, said gas-producing agent can be combined before, during, or after delivery of the emulsion in vivo. The produced gas may be inert, or may have biological or therapeutic properties. A gas-producing agent can comprise but is not limited to nitroglycerin, amyl nitrite, nitrosothiol, isosorbide dinitrate, nitrosoacetylamine, and nitrosocysteine (nitric oxide gas precursors); NONOate's (nitroxyl gas precursors); aluminum sulfide and sodium hydrosulfide (hydrogen sulfide gas precursors); ammonium hydrosulfide (hydrosulfide gas precursor); thionitrous ester (thionitrous acid gas precursor); carbon/zinc oxide and carbon monoxide releasing molecules (carbon monoxide gas precursors); sodium carbonate and citric acid (carbon dioxide gas precursors); and calcium hypochlorite (hypochlorous acid gas precursor).

In another embodiment, the described emulsion can be mixed with a leachable pore-forming material that produces pores during the drying or hardening of the TFE copolymer emulsion to form a sponge-like material. In an embodiment, said leachable pore-form ing agent can be combined before, during, or after delivery of the emulsion in vivo. A leachable pore-forming agent can comprise but is not limited to particles of sodium chloride, glucose, sucrose, bioabsorbable material, collagen, albumin, hydroxyapatite, lipids, polyethylene glycol, polyvinyl alcohol, and the like.

In various embodiments, the described emulsion can be used to add lubricity to various materials by imbibing or mixing therewith or function as a lubricating fluid.

In another embodiment, the described emulsion can be combined with other materials and used to coat, fill or re-fill a tissue, organ, or medical device with a therapeutic agent. Thus, the emulsion can be used to form a drug depot—capable of controlled drug delivery to the surrounding tissue or organ. For example, the emulsion can comprise a sclerosing agent that can be used to compromise a cell(s) or tissue, e.g., denervate a renal nerve. In various embodiments, the emulsion can be injected about the renal artery proximate to the renal nerve. In various embodiments, the solvent phase can comprise the sclerosing agent, such as ethanol.

In an embodiment, an application can be forming a structural member, such as a cast. The described emulsion can be formed into a desired shape. Reinforcing elements can optionally be mixed with the emulsion. Structural forms can optionally be utilized to receive the emulsion and give the hardened emulsion a desired shape. The emulsion, as the solvents evaporate, can harden to form a structural member.

Another embodiment of the disclosure comprises a stable, water-in-solvent emulsion comprising: a solvent phase comprising a fluorinated copolymer and a water miscible organic solvent, an aqueous phase comprising a water-soluble agent and water, wherein the mass ratio of the solvent phase to the aqueous phase ranges from about 99 to 1 to about 1 to 1. Another embodiment of the disclosure comprises a stable, water-in-solvent emulsion comprising: a solvent phase comprising a fluorinated copolymer, a therapeutic agent, and a water miscible organic solvent, and an aqueous phase comprising water, wherein the mass ratio of the solvent phase to the aqueous phase ranges from about 99 to 1 to about 1 to 1. In another embodiment, said therapeutic agent is a hydrophobic therapeutic agent, pharmaceutical, or drug. In various embodiments, said copolymer comprises tetrafluoroethylene. In addition, the second monomer can comprise functional groups from the group selected from acetate, alcohol, amine and amide, and combinations thereof. In another embodiment, said fluorinated copolymer is TFE-VAc. In another embodiment, said fluorinated copolymer is TFE-VOH. In another embodiment, said water miscible organic solvent is selected from the group shown in Table 1. In another embodiment, said water miscible organic solvent is selected from the group consisting of alcohols, esters, ketones, glycols, and aldehydes, and polar aprotic solvents. In another embodiment, the mass ratio of the solvent phase to the aqueous phase range is from about 15:1 to about 1:1.

Another embodiment of the disclosure comprises a water-in-solvent emulsion comprising a continuous phase comprising an a fluorinated copolymer and a water miscible organic solvent, and a discontinuous aqueous phase comprising a water soluble agent and water; wherein the mass ratio of the solvent phase to the aqueous phase ranges from about 99 to 1 to about 1 to 1. Another embodiment of the disclosure comprises a water-in-solvent emulsion comprising a continuous phase comprising an a fluorinated copolymer, a therapeutic agent, and a water miscible organic solvent, and a discontinuous aqueous phase comprising water; wherein the mass ratio of the solvent phase to the aqueous phase ranges from about 99 to 1 to about 1 to 1. In another embodiment, said therapeutic agent is a hydrophobic therapeutic agent, pharmaceutical, or drug. In various embodiments, said copolymer comprises tetrafluoroethylene. In addition, said fluorinated copolymer comprises functional groups selected from the group consisting of acetate, alcohol, amine and amide, and combinations thereof. In another embodiment, said fluorinated copolymer is TFE-VAc. In another embodiment, said fluorinated copolymer is TFE-VOH. In another embodiment, said water miscible organic solvent is selected from the group shown in Table 1. In another embodiment, said water miscible organic solvent is selected from the group consisting of alcohols, esters, ketones, glycols, and aldehydes, and polar aprotic solvents. In another embodiment, the mass ratio of the solvent phase to the aqueous phase range is from about 15:1 to about 1:1.

Another embodiment of the disclosure comprises a method for coating a substrate comprising applying a water-in-solvent emulsion to said substrate, wherein said water-in-solvent emulsion comprises a fluorinated copolymer, a solvent phase comprising a water miscible organic solvent, a water soluble agent, a water phase, wherein said emulsion is kinetically stable; and allowing said organic solvent and water to evaporate. Another embodiment of the disclosure comprises a method for coating a substrate comprising applying a water-in-solvent emulsion to said substrate, wherein said water-in-solvent emulsion comprises a fluorinated copolymer, a therapeutic agent, a solvent phase comprising a water miscible organic solvent, and a water phase, wherein said emulsion is kinetically stable, and allowing said organic solvent and water to evaporate. In various embodiments, said copolymer comprises tetrafluoroethylene. In addition, said fluorinated copolymer comprises functional groups selected from the group consisting of acetate, alcohol, amine and amide, and combination thereof. In another embodiment, said fluorinated copolymer is TFE-VAc. In another embodiment, said fluorinated copolymer is TFE-VOH. In another embodiment, said substrate is selected from the group consisting of a medical device, a living organ, and a living tissue, and their combinations. In another embodiment, said substrate is a medical device. In another embodiment, said medical device is selected from the group consisting of a vascular graft, stent, stent graft, vascular patch, soft tissue patch, heart valve, suture, angioplasty balloon, embolic filter, catheter and an implantable pacing lead. In another embodiment, said medical device has a single use application. In another embodiment, said emulsion is capable of being applied onto a medical device using a single applicator. In another embodiment, said single applicator is a single spray nozzle (or other single applicator such as needle tips, catheter tips, dispenser, pipet, and the like). In another embodiment, said emulsion is not stirred or agitated during application onto said substrate. In another embodiment, said water-in-solvent emulsion is applied to a substrate and the water miscible organic solvent and water are removed (through evaporation or drying) leaving a dry coating comprising the fluorinated copolymer and a water-soluble agent on the substrate. In another embodiment, said water-in-solvent emulsion is applied to a substrate and the water miscible organic solvent and water are removed (through evaporation or drying) leaving a dry coating comprising the fluorinated copolymer and a water-soluble agent distributed evenly on said substrate. In another embodiment, said water-in-solvent emulsion is applied to a substrate, the water miscible organic solvent is removed (through partial evaporation, extraction, or leaching) to harden the emulsion, leaving a hydrated coating comprising the fluorinated copolymer and a water-soluble agent on the substrate. In another embodiment, said a fluorinated copolymer and a water-soluble agent are evenly distributed on said substrate. In another embodiment, said water-soluble agent is a therapeutic agent, pharmaceutical, or drug. In another embodiment, said a fluorinated copolymer and a therapeutic agent are evenly distributed on said substrate. In another embodiment, said therapeutic agent is a hydrophobic therapeutic agent, pharmaceutical, or drug. In another embodiment, said medical device is dip coated into said emulsion. In another embodiment, said emulsion is applied to said substrate by painting, pipetting, coating, spraying, or brushing techniques.

Another embodiment of the disclosure comprises a bulking or filler material comprising a fluorinated copolymer, a solvent phase comprising a water miscible organic solvent, a water-soluble agent, and a water phase; wherein when said components are mixed, a kinetically stable emulsion is formed. Another embodiment of the disclosure comprises a bulking or filler material comprising a fluorinated copolymer, a solvent phase comprising a water miscible organic solvent, a therapeutic agent, and a water phase; wherein when said components are mixed, a kinetically stable emulsion is formed. In various embodiments, said copolymer comprises tetrafluoroethylene. In addition, said fluorinated copolymer comprises functional groups selected from the group consisting of acetate, alcohol, amine and amide, and combinations thereof. In another embodiment, said fluorinated copolymer is TFE-VAc. In another embodiment, said fluorinated copolymer is TFE-VOH. In another embodiment, said water-soluble agent is a therapeutic agent, pharmaceutical, or drug. In another embodiment, said therapeutic agent is hydrophobic. In various embodiments, said emulsion is capable of being inserted, injected, or otherwise placed into a medical device. In various embodiments, medical devices include an injectable or fillable casing of any desired shape, e.g., a tubular, circular, or pillow like shape. Said emulsion can fill a medical device in vivo. In other embodiments, said emulsion is capable of being inserted, injected, or otherwise placed into a tissue, an empty space, gap, or defect surrounded by tissue, a lumen of a vessel, or a complex system of vessels (collectively, "occlusion site" or "bulking site"). Said emulsion can be inserted into a medical device and/or an occlusion site using a single applicator and/or injector. Said single applicator can be a single spray nozzle, needle, catheter, or the like. In another embodiment, said emulsion remains kinetically stable, requiring neither mixing nor agitation during introduction into a medical device and/or occlusion site. In another embodiment, said water-in-solvent emulsion is introduced into said medical device and/or occlusion site and the water miscible organic solvent and water are removed (through leaching) leaving a hardened polymeric mass comprising the fluorinated copolymer and a water-soluble agent. In another embodiment, said water-in-solvent emulsion is introduced into said medical device and/or occlusion site and the water miscible organic solvent and water are removed (through leaching) leaving a hardened polymeric mass comprising the fluorinated copolymer and a therapeutic agent. In another embodiment, said water-in-solvent emulsion is introduced into said medical device and/or occlusion site and the water miscible organic solvent and water are removed (through leaching) leaving a hardened polymeric mass comprising the fluorinated copolymer and a water-soluble agent distributed evenly throughout said mass. In another embodiment, said water-in-solvent emulsion is introduced into said medical device and/or occlusion site and the water miscible organic solvent is removed (through leaching) leaving a hardened, hydrated mass comprising the fluorinated copolymer and a water-soluble agent. In another embodiment, said fluorinated copolymer and a water-soluble agent are evenly distributed throughout a polymeric mass. In another embodiment, said fluorinated copolymer and a therapeutic agent are evenly distributed throughout a polymeric mass. In another embodiment, said medical device is selected from the group consisting of an injectable or fillable casing, a vascular graft, stent, stent graft, vascular patch, soft tissue patch, heart valve, suture, angioplasty balloon, embolic filter, catheter, and an implantable pacing lead. In another embodiment, said water miscible organic solvent is selected from the group shown in Table 1 (see below). In another embodiment, said water miscible organic solvent is selected from the group consisting of alcohols, esters, ketones, glycols, and aldehydes, and polar aprotic solvents.

Another embodiment of the disclosure comprises a method of preparing a water-in-solvent emulsion comprising the steps of, dissolving a fluorinated copolymer in a water miscible organic solvent to form a first phase, dissolving a water-soluble agent in water to form a second phase, and combining the first phase with the second phase such that the emulsion is kinetically stable. Another embodiment of the disclosure comprises a method of preparing a water-in-solvent emulsion comprising the steps of, dissolving a fluorinated copolymer and a therapeutic agent in a water miscible organic solvent to form a first phase, providing water to form a second phase, and combining the first phase with the second phase such that the emulsion is kinetically stable. In various embodiments, said copolymer comprises tetrafluoroethylene. In addition, said fluorinated copolymer comprises functional groups selected from the group consisting of acetate, alcohol, amine and amide, and combinations thereof. In another embodiment, said fluorinated copolymer is TFE-VAc. In another embodiment, said fluorinated copolymer is TFE-VOH.

Another embodiment of the disclosure comprises a method of preparing a water-in-solvent emulsion comprising the steps of dissolving a fluorinated copolymer in a water miscible organic solvent to form a first phase, dissolving a water-soluble agent in water to form a second phase, and combining the first phase with the second phase at a ratio of 99:1 to 1:1 such that the emulsion is kinetically stable. Another embodiment of the disclosure comprises a method of preparing a water-in-solvent emulsion comprising the steps of dissolving a fluorinated copolymer and a therapeutic agent in a water miscible organic solvent to form a first phase, providing water to form a second phase, and combining the first phase with the second phase at a ratio of 99:1 to 1:1 such that the emulsion is kinetically stable. In various embodiments, said copolymer comprises tetrafluoroethylene. In addition, said fluorinated copolymer comprises functional groups selected from the group consisting of acetate, alcohol, amine and amide, and combinations thereof. In another embodiment, said fluorinated copolymer is TFE-VAc. In another embodiment, said fluorinated copolymer is TFE-VOH.

Another embodiment of the disclosure comprises a method of coating a substrate comprising a water-in-solvent emulsion comprising the steps of providing a water-in-solvent emulsion comprising, a fluorinated copolymer, a solvent phase comprising a water miscible organic solvent, a water soluble agent, water phase, wherein said emulsion is kinetically stable, and applying the emulsion to the substrate. Another embodiment of the disclosure comprises a method of coating a substrate comprising a water-in-solvent emulsion comprising the steps of providing a water-in-solvent emulsion comprising, a fluorinated copolymer, a therapeutic agent, a solvent phase comprising a water miscible organic solvent, and a water phase, wherein said emulsion is kinetically stable, and applying the emulsion to the substrate. The solvent, and optionally the water, can subsequently be removed through evaporation, extraction, or leaching. In another embodiment, the substrate can comprise a tissue upon which said emulsion can be applied, such as through spraying, to form a temporary or permanent coating, graft, or patch. For example, the substrate can be the intima or adventitia of a vessel, ureter, intestine, or esophagus. A spray head providing a radial, circumferential spray pattern on the distal end of a catheter can be used to apply the emulsion to the surrounding intima or adventitia. Similarly, the substrate can comprise a medical device to form a coating thereon. Said emulsion can be applied to a substrate with the use of an applicator. In another embodiment, said emulsion is applied to said substrate by painting, pipetting, coating, spraying, or brushing techniques.

Another embodiment of the disclosure comprises a method of coating a substrate comprising a water-in-solvent emulsion comprising the steps of providing a water-in-solvent emulsion comprising a fluorinated copolymer, a solvent phase comprising a water miscible organic solvent, a water soluble agent, a water phase, wherein said emulsion is kinetically stable, and applying the emulsion to the substrate and removing the solvent and water, wherein the soluble agent phase is less than about 500 nm as measured by Raman spectroscopy. Another embodiment of the disclosure comprises a method of coating a substrate comprising a water-in-solvent emulsion comprising the steps of providing a water-in-solvent emulsion comprising a fluorinated copolymer, a solvent phase comprising a water miscible organic solvent, a water soluble agent, a water phase, wherein said emulsion is kinetically stable, and applying the emulsion to the substrate and removing the solvent and water, wherein the soluble agent phase is molecularly mixed as measured by M-DSC. Another embodiment of the disclosure comprises a method of coating a substrate comprising a water-in-solvent emulsion comprising the steps of providing a water-in-solvent emulsion comprising a fluorinated copolymer, a therapeutic agent, a solvent phase comprising a water miscible organic solvent, a water phase, wherein said emulsion is kinetically stable, and applying the emulsion to the substrate and removing the solvent and water, wherein the soluble agent phase is less than about 500 nm as measured by Raman spectroscopy. Another embodiment of the disclosure comprises a method of coating a substrate comprising a water-in-solvent emulsion comprising the steps of providing a water-in-solvent emulsion comprising a fluorinated copolymer, a therapeutic agent, a solvent phase comprising a water miscible organic solvent, a water phase, wherein said emulsion is kinetically stable, and applying the emulsion to the substrate and removing the solvent and water, wherein the soluble agent phase is molecularly mixed as measured by M-DSC. In various embodiments, said copolymer comprises tetrafluoroethylene. In addition, said fluorinated copolymer comprises functional groups selected from the group consisting of acetate, alcohol, amine and amide, and combinations thereof. In another embodiment, said fluorinated copolymer is TFE-VAc. In another embodiment, said fluorinated copolymer is TFE-VOH.

Further embodiments described herein include systems or kits comprising an emulsion as described herein and a delivery device. In some embodiments, delivery devices comprise an implantation guide, which facilitates delivery of said emulsion to an implantation site by providing a delivery path. In other embodiments, delivery devices comprise an implantation guide and a translating and/or rotating member, wherein the translating and/or rotating member facilitates translation of said emulsion along the delivery path defined by the implantation guide. Translating member embodiments include a syringe, an implantation piston member, or any other device that facilitates translation of said emulsion along the delivery path.

Figure 2A:
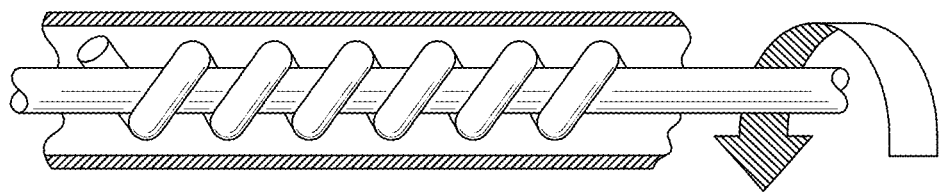
FIG. 2(a) illustrates a delivery device embodiment comprising an auger member.
Figure 2B:
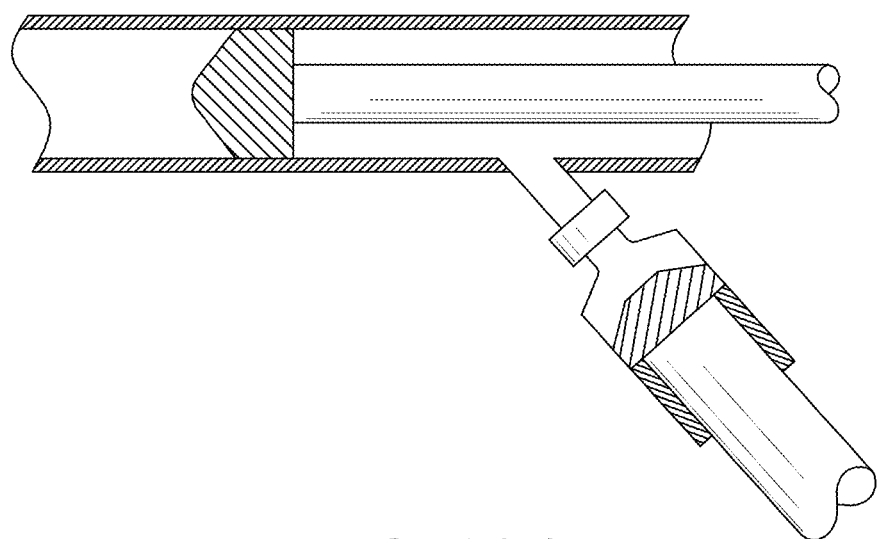
FIG. 2(b) illustrates a delivery device embodiment comprising a plurality of syringe devices.
Figure 3A:
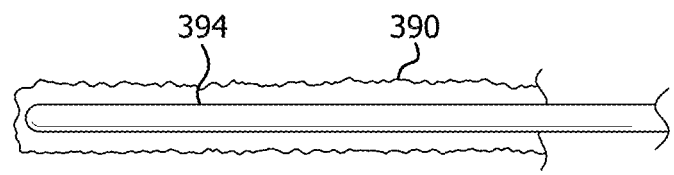
FIGS. 3(a) to 3(d) illustrate an occlusive casing device being filled with an emulsion as described herein.
Figure 3B:
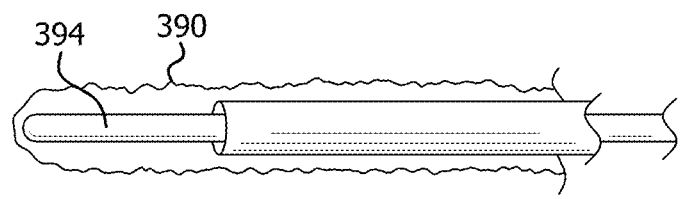
Figure 3C:
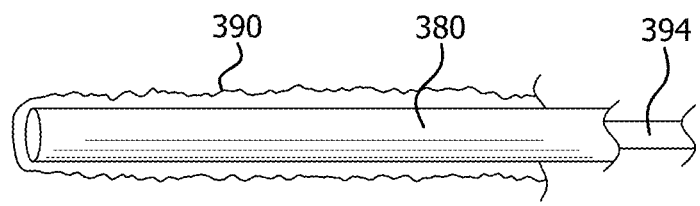
Figure 3D:
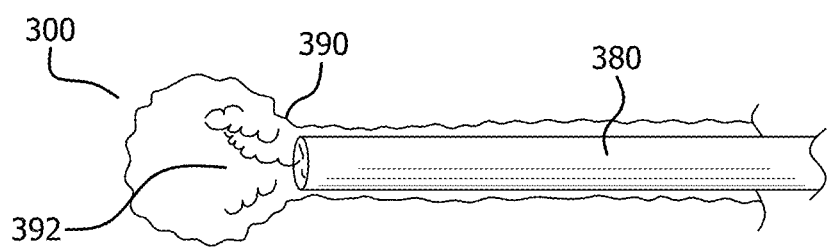
Figure 3E:
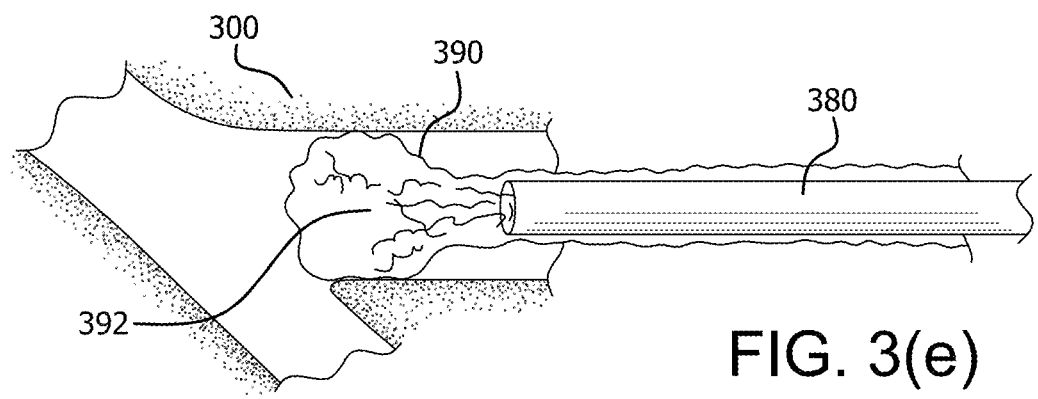
FIG. 3(e) illustrates FIG. 3(d) in vivo.

With reference to FIG. 2(b), a delivery device comprising a translating member comprises at least one syringe device. A syringe can be used to inject an amount of said emulsion into an elongate member comprising a lumen. Then, a plunger can be used to push the emulsion through the lumen and toward an implantation site. The plunger can be withdrawn and the process repeated, if desired. A plunger seal can comprise a one-way seal so that upon withdrawal of the plunger, said emulsion is not also withdrawn. In another embodiment, a delivery device can also comprise components that apply a mechanical advantage at the syringe, such as a screw, a lever, a hydraulic device, or the like.

In other embodiments, a delivery device can comprise a rotating member. Rotating member embodiments can include an auger member or any other rotating device that facilitates translation of said emulsion. With reference to FIG. 2(a), an auger delivery device embodiment is illustrated. Rotating auger member comprises a corkscrew shaped structure housed within at least a portion of a lumen of an elongate member and can be used to facilitate delivery of the emulsions as described herein.

In an embodiment, a delivery device for coating a substrate with an emulsion formula described herein can also comprise a spray atomizer, aerosol, air brush, or the like. In an embodiment, said atomizer, airbrush or the like can have any desired spray pattern, e.g., a full cone, hollow cone, flat spray, or radial spray pattern.

Figure 10:
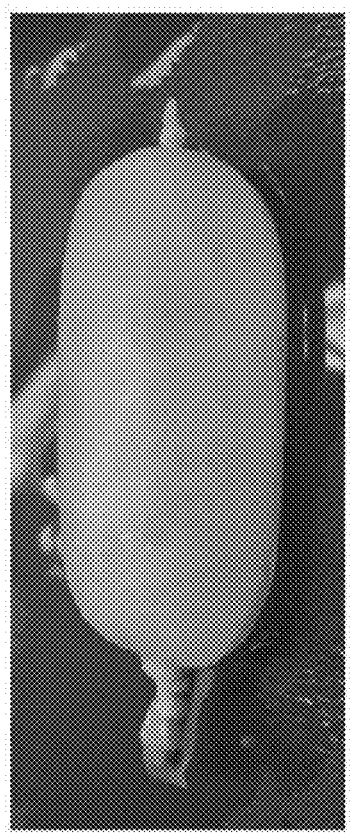
FIG. 10 depicts an occlusive casing embodiment filled with an emulsion as described herein.
Figure 11A:
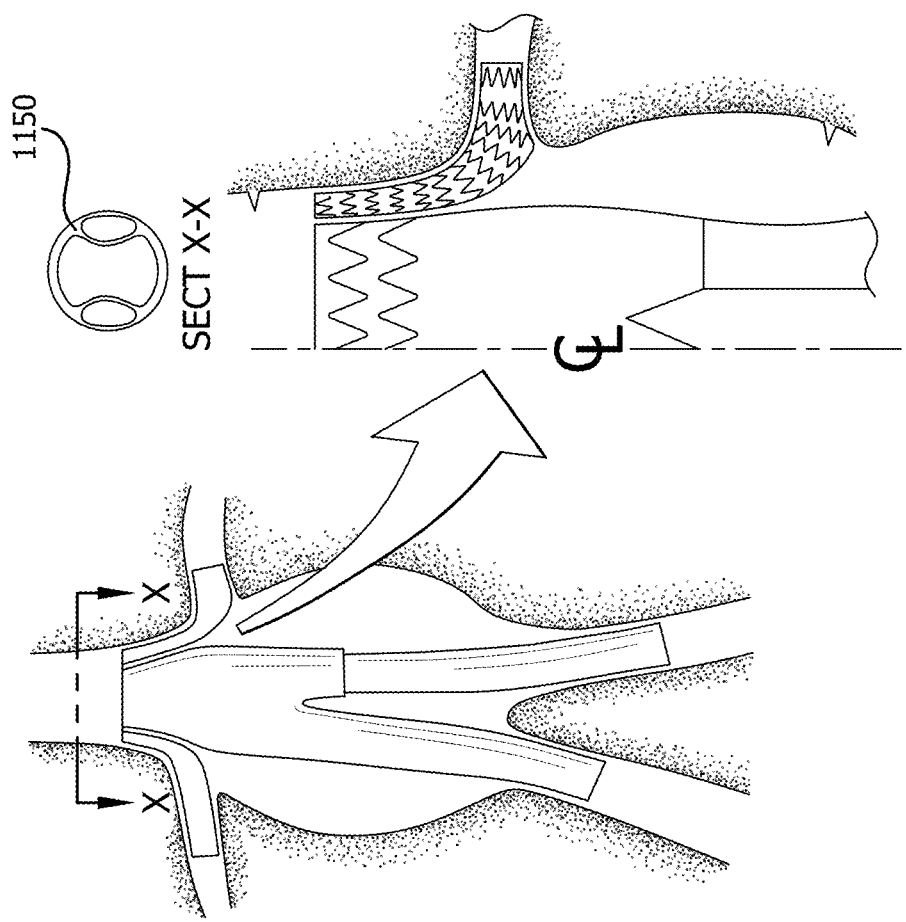
FIGS. 11(a) through 11(f) illustrate the steps to seal an endoleak with an emulsion as described in the present disclosure.
Figure 11C:
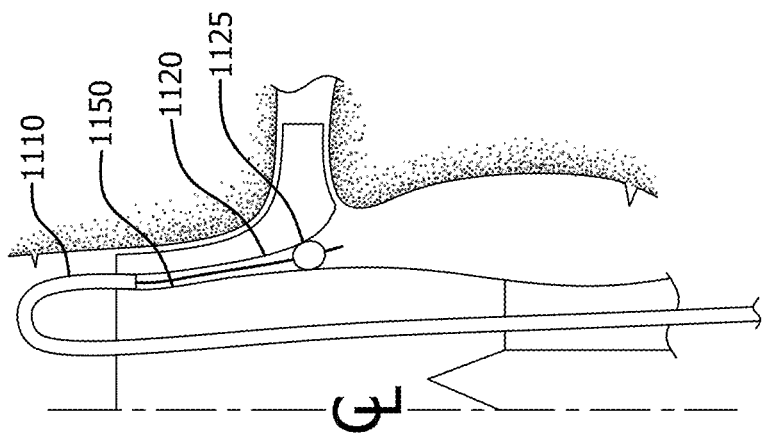
Figure 11B:
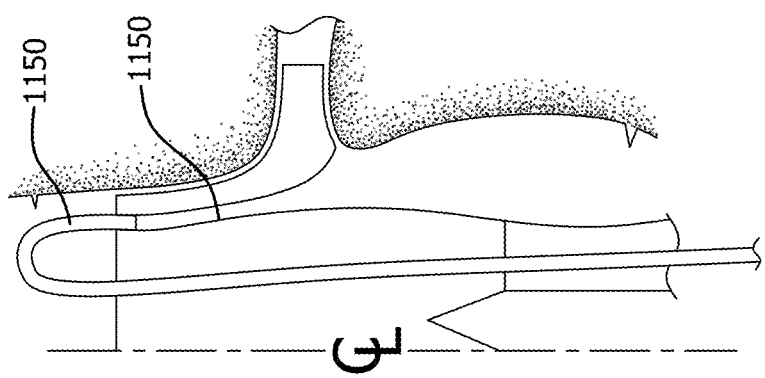
Figure 11D:
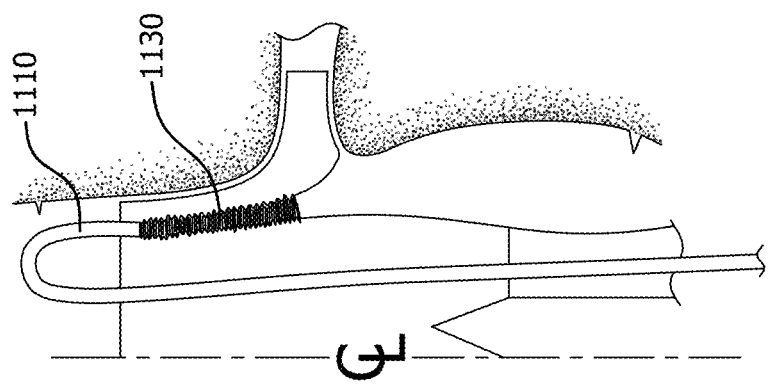
Figure 11E:
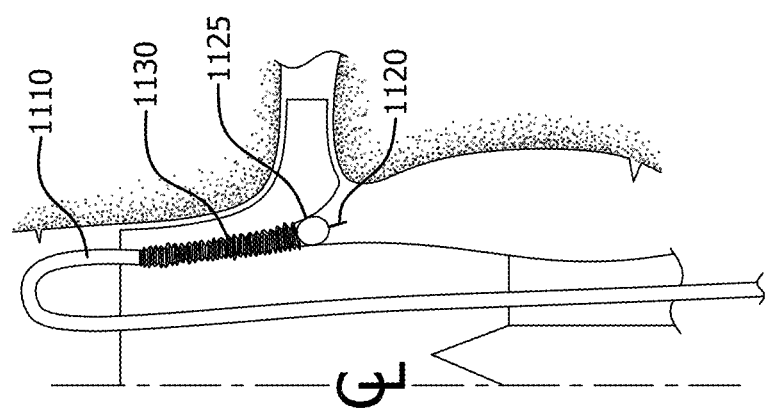
Figure 11F:
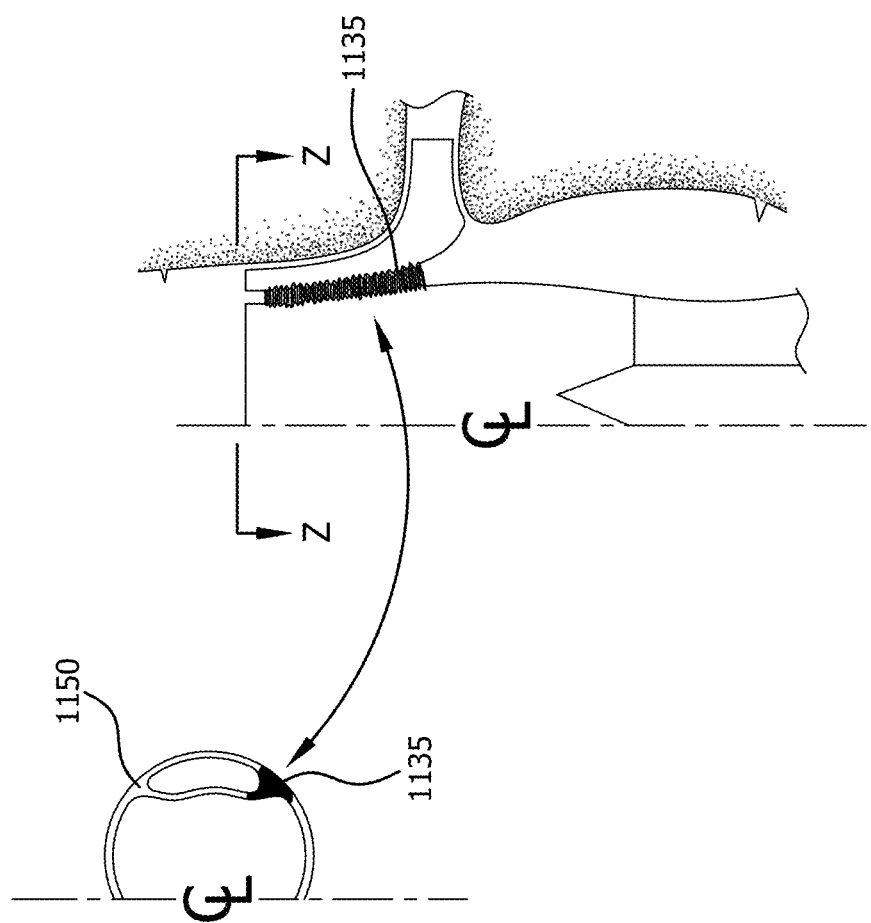

In an embodiment, with reference to FIG. 10, a delivery device for coating a substrate with an emulsion formula can also comprise a perfusable balloon. The balloon can be inflated with an emulsion, and the balloon material is configured to allow an emulsion to perfuse through the balloon wall or an outer balloon layer. In another embodiment, the balloon material can comprise a membrane of a microporous material configured to allow the emulsion to pass through its walls. Examples of such microporous materials include polymer comprising fibrillated microstructure such as expanded polytetrafluoroethylene. In another embodiment, the material can comprise a film or sheet material that has micropores. In another embodiment, the balloon material can comprise microvalves.

With reference to FIGS. 3(a) to 3(e), another embodiment comprises the emulsions as described herein insertable into an occlusive casing. Said occlusive casing 390 can comprise any structure defining a lumen or a cavity that can be filled or injected with an emulsion. Occlusive casing 390 and emulsion combination can be utilized for tissue bulking, filling an empty space, gap, or defect surrounded by tissue, or occluding the lumen of a vessel.

In an embodiment, an occlusive casing can distend or expand to occupy and approximately conform to the lumen of a vessel or other surrounding empty space. For example, occlusive casing 390 can have a pleated or knitted conformation, which can expand upon introduction of said emulsion. In other embodiments, occlusive casing 390 can comprise a flexible material that stretches and/or expands upon introduction of said emulsion. In addition, occlusive casing 390 can comprise a distensible and compliant film or fabric to facilitate approximately conforming to the surrounding space. Alternatively or in addition thereto, occlusive casing 390 can occupy a volume by bending and folding on it self as it is injected with said emulsion, creating a convoluted mass of emulsion contained within occlusive casing 390.

Occlusive casing 390 can be any shape or material suitable for occluding the desired lumen or body cavity. Examples of shapes include spherical or oval, tubular, conical, pillow-shaped, or any other shape suitable for the application. By way of example, occlusive casing 390 can comprise a distensible sleeve. A distensible sleeve comprises a generally tubular shape having a proximal and distal end and a lumen therethrough. The distal end can be permanently closed to contain said emulsion 392 as it is introduced. Implantation guide 380 can be inserted through the proximal end to deliver said emulsion 392.

In order to close occlusive casing 390 so that occlusive material 392 does not leak from occlusive casing 390 once implantation guide 380 is withdrawn, occlusive casing 390 can be self-sealing or comprise a closure in order to at least substantially close the proximal end upon withdrawal of guide 380. Closure can comprise any mechanism or configuration that will close the proximal end of occlusive casing 390. For example, closure can comprise self-collapsing section of occlusive casing 390, such as an elastic band that will collapse down and close the proximal end of the occlusive casing 390 upon retraction of implantation guide 380. Other closure embodiments can include a purse string, clip, ligature, or the like.

Similarly, occlusive casing 390 can comprise a film or fabric that substantially prevents passage of said emulsion through the casing. In an embodiment, the film or fabric is configured such that apertures, m icroporous structure, spaces between woven or knitted elements do not exceed a desired size, e.g., 100 μm. Nevertheless, occlusive casing 390 can also have a sufficiently permeable material to allow passage of a therapeutic agent to the surrounding environment as it leaches or diffuses from the polymeric mass.

In an embodiment, wherein said emulsion 392 comprises a therapeutic agent, the transfer of the therapeutic agent may need to be restricted to permeating through only certain portions of occlusive casing 390. Accordingly, occlusive casing 390 can comprise sections or areas that remain impermeable to a therapeutic agent at least during the initial introduction into a lumen, gap, or tissue. For example, having an impermeable end cap(s) on occlusive casing 390 can mitigate undesired permeation of a therapeutic agent. Areas of occlusive casing 390 can be made impermeable by coating with a biocompatible sealant such as copolymers of lactic acid and glycolic acid (PLA/PGA), or by varying the microstructure or thickness in these areas to make less permeable.

In accordance with another embodiment, a method of delivering occluding device 300 can comprise the steps of inserting occlusive casing 390 on guidewire 394 into a vessel; passing implantation guide 380 over guidewire 394 and into lumen of occlusive casing 390; and injecting said emulsion 392 into lumen of occlusive casing 390. Implantation guide 380 can be retracted as it injects.

While particular embodiments of the present disclosure have been illustrated and described herein, the present disclosure should not be limited to such illustrations and descriptions. It should be apparent that changes and modifications could be incorporated and embodied as part of the present disclosure within the scope of the following claims. The following examples are further offered to illustrate the present disclosure.

EXAMPLES

Example 1

Syntheses of Copolymers Comprising Tetrafluoroethylene and Functional Groups Comprising Acetate (TFE-VAc)

Copolymers comprising varying mole ratios of vinyl acetate to tetrafluoroethylene (VAc:TFE) were prepared according the following general synthetic scheme. To a nitrogen purged 1 L pressure reactor under vacuum were added 500 g DI water, 2.0 g of 20% aqueous ammonium perfluorooctanoate, 30 ml of distilled vinyl acetate, 10 g of n-butanol, and 0.2 g of ammonium persulfate. Tetrafluoroethylene monomer was then fed into the reactor until the reactor pressure reached 1500 KPa. The mixture was stirred and heated to 50° C. When a pressure drop was observed, 25 ml of additional vinyl acetate was slowly fed into the reactor. The reaction was stopped when the pressure dropped another 150 KPa after vinyl acetate addition. The copolymer was obtained from freeze-thaw coagulation of the latex emulsion and cleaned with methanol/water extraction. The copolymers' composition and molecular weight are listed in Table 3.

TABLE 3

Copolymer composition and molecular weight.

| Copolymer # | VAc mole % | TFE mole % | MW (KDa) |
|---|---|---|---|
| 100-0 | 80.0 | 20.0 | 300 |
| 100-1 | 81.1 | 18.9 | 337 |
| 100-2 | 81.2 | 18.8 | 220 |
| 100-3 | 84.5 | 15.5 | 430 |
| 100-4 | 76.5 | 23.5 | 122 |

Example 2

This Example Describes the Preparation and Use of a Suspension of a Water-Soluble Drug in a Non-Aqueous Fluoropolymer Solution and the Inherent Difficulty Associated with Using Said Suspension to Coat a Substrate A solution (referred herein as Solution D) was prepared by dissolving 0.10 g of a copolymer of tetrafluoroethylene and perfluoromethyl vinyl ether ("PATT-D"), as described in U.S. Patent Application Publication 2006/0198866 (WL Gore & Associates, Inc, Lot CV30V-0203) in 100 g of Fluorinert FC77 (3M, St. Paul, Minn.).

A suspension (referred herein as Suspension D) was formed by adding 0.27 g dexamethasone sodium phosphate (DSP) (Spectrum, Gardena, Calif.) to Solution D. The resulting Suspension D contained approximately 99.63% FC77, 0.27% DSP, and 0.10% PATT-D (g per g total suspension). The theoretical solids loadings (g per g total solids) of DSP and PATT-D in this suspension were 73% and 27%, respectively. Suspension D was stirred for approximately 1 hour (hr) using a conventional stir plate. While stirring, DSP aggregates were visible in Suspension D, as Fluorinert is a nonsolvent for DSP. When stirring was halted, the DSP immediately (within 30 seconds) precipitated to the bottom of the storage vessel, as depicted in FIGS. 4a and 5(a)(i), demonstrating the inherent kinetic instability of the suspension (DSP aggregates represented schematically in FIG. 5(a)(ii)).

A film of expanded polytetrafluoroethylene (WL Gore & Associates, Inc.) was fixed to a flat surface. Suspension D was pumped through a 30 psig, atomizing spray, nozzle (Spraying Systems Co., Laguna Hills, Calif.) at 10 ml/min. The spray nozzle became obstructed within 30 seconds. Five circular film samples (DS1 through DS5; 15.5 mm in diameter) were cut from the coated film.

Samples DS1 through DS3 (DS1-3) were analyzed for DSP loading by the following steps. First, all samples were weighed. To estimate the total coating mass applied, the mass of samples DS1-3 was compared to the average mass of uncoated film samples of equal size. The average coating mass of samples DS1-3 was 0±0 μg/$cm^2$. Since the spray nozzle became clogged, little to no coating was deposited on the ePTFE film.

Then, samples DS1-3 were placed in separate vials containing 3 ml phosphate buffered saline (PBS) (0.15M NaCl, pH 7.4, Invitrogen Corporation Carlsbad, Calif.). The samples remained in the PBS for 72 hours. After this time, any DSP in the PBS supernatant of each sample was analyzed by measuring UV absorption at 242 nm. Specifically, standards of known amounts of DSP in PBS were prepared and analyzed by UV spectroscopy. A linear standard curve of absorbance at 242 nm vs. DSP concentration was then generated. Absorbance within the supernatant of each sample was then compared to the standard curve in order to calculate DSP concentration. Average DSP loading in the film samples DS1-3 was 0±0 μg/$cm^2$ (FIG. 6) indicating essentially no DSP present in the coating.

Scanning electron microscopy (SEM) was used to image a sample (Sample DS5) of coated film. As shown of FIG. 7(*b*), an occasional DSP aggregate could be seen on the film (but below the detectable limits of UV spectroscopy), but otherwise the film appeared essentially uncoated with DSP.

As these results indicate, kinetically unstable suspensions of a fluoropolymer dissolved in a fluorinated solvent with a water-soluble drug can be inherently difficult to use in coating a substrate since these suspensions result in particle settling and obstruction of coating nozzles. As a results, drug is not coated/deposited onto the substrate.

Example 3

This Example Describes the Preparation and Use of a Suspension of a Water-Soluble Drug in a Non-Aqueous Fluorinated Copolymer Solution and the Inherent Difficulty Associated with Using Said Suspension to Coat a Substrate A solution (referred herein as Solution V) was prepared by dissolving 0.10 g poly(tetrafluoroethylene-co-vinyl acetate) (TFE-VAc) (as synthesized according to Example 1, #100-0) in 100 g acetone (Sigma Aldrich, St. Louis, Mo.).

A suspension (referred herein as Suspension V) was formed by adding 0.27 g dexamethasone sodium phosphate (DSP) (Spectrum, Gardena, Calif.) DSP to Solution V. The resulting Suspension V contained approximately 99.63% acetone, 0.27% DSP, and 0.10% TFE-VAc (g per g total suspension). The theoretical solids loadings (g per g total solids) of DSP and TFE-VAc in this suspension were 73% and 27%, respectively. Suspension V was stirred for approximately 1 hr using a conventional stir plate. While stirring, DSP aggregates were visible in Suspension V, as acetone is a nonsolvent for DSP. When stirring was halted, the DSP immediately (within 30 seconds) precipitated to the bottom of the storage vessel (FIGS. 4*b* and 5(*b*)(*i*)) demonstrating the inherent kinetic instability of the suspension (DSP precipitates represented schematically in FIG. 5(*b*)(*ii*)).

A film of expanded polytetrafluoroethylene (WL Gore & Associates, Inc.) was fixed to a flat surface. Suspension V was pumped through a 30 psig, atomizing spray, nozzle (Spraying Systems Co., Laguna Hills, Calif.) at 10 ml/min for approximately 10 min. Five circular film samples (VS1 through VS5; 15.5 mm in diameter) were cut from the coated film.

Samples VS1 through VS3 (VS1-3) were analyzed for DSP loading by the following steps. First, all samples were weighed. To estimate the total coating mass applied, the mass of samples VS1-3 was compared to the average mass of uncoated film samples of equal size. The average coating mass of samples VS1-3 was 485.62±17.23 µg/cm$^2$.

Figure 6A:
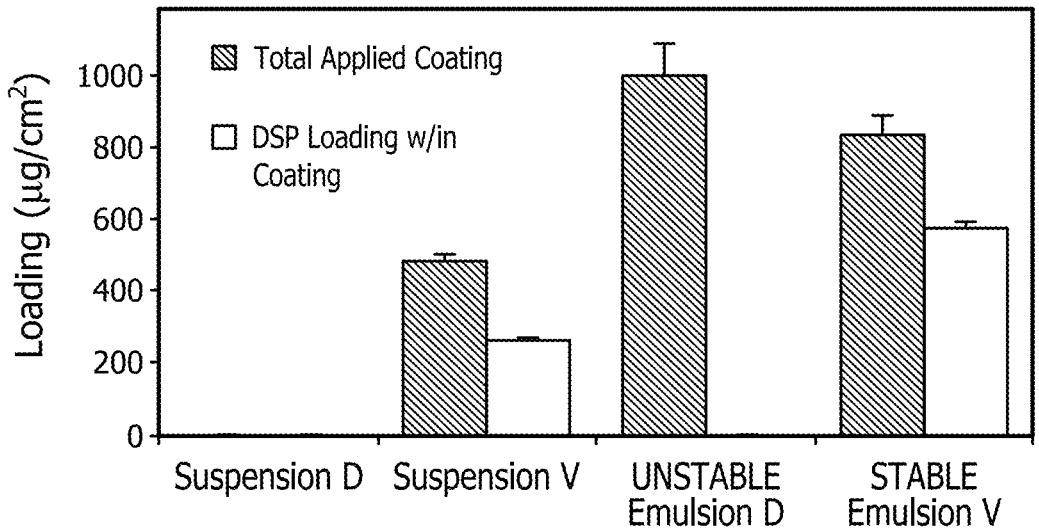
FIG. 6(a) depicts the total coating mass and drug loading (μg/cm$^2$) in film samples coated with Suspension D, Suspension V, Kinetically Unstable Emulsion D, or Kinetically Stable Emulsion V, as described in the Examples.

Then, samples VS1-3 were then placed in separate vials containing 3 ml phosphate buffered saline (PBS) (0.15M NaCl, pH 7.4, Invitrogen Corporation Carlsbad, Calif.). The samples remained in the PBS for 72 hours. After this time, DSP in the PBS supernatant was analyzed by measuring UV absorption at 242 nm. Specifically, standards of known amounts of DSP in PBS were prepared and analyzed by UV spectroscopy. A linear standard curve of absorbance at 242 nm vs. DSP concentration was then generated. Absorbance within the supernatant of each sample was then compared to the standard curve in order to calculate DSP concentration. Average DSP loading in the film samples was 265.97±4.16 µg/cm$^2$ as depicted in FIG. 6(a) (55% of the total coating mass, FIG. 6(b)).

Figure 7A:
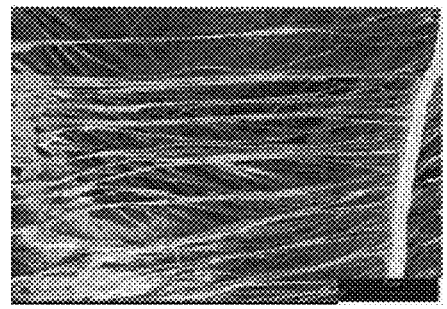
FIGS. 7(a) through 7(e) depict SEM micrographs of (a) uncoated film, and film coated with (b) Suspension D, (c) Suspension V, (d) Kinetically Unstable Emulsion D, (e) Kinetically Stable Emulsion V, as described in the Examples.
Figure 7B:
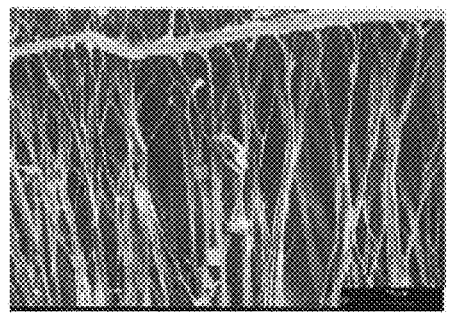
Figure 7C:
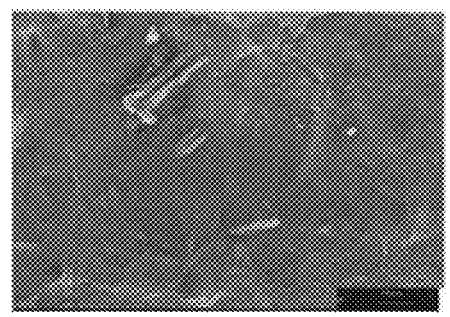
Figure 7D:
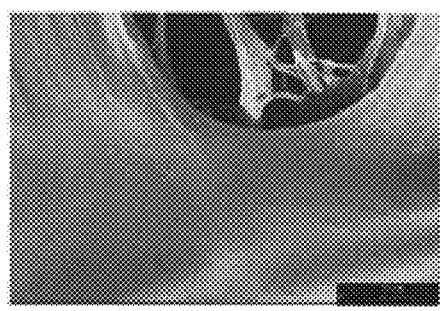

Scanning electron microscopy (SEM) was used to image a sample (Sample VS5) of coated film (FIG. 7c). As shown of FIG. 7c, the film had an inhomogeneous appearance indicating that the surface uniformity of the drug content was not consistent on a microscale (larger than the approximately 10 micrometer drug particles). A dense polymer layer with DSP aggregates was seen on the film.

As these results indicate, kinetically unstable suspensions of a fluoropolymer dissolved in an organic Class III solvent with a water-soluble drug can be inherently difficult to use in coatings. When Suspension V was used to coat a film, the resulting coating contained only 55% DSP. This loading was less than the theoretical DSP loading (73%) in the suspension. Additionally, Suspension V resulted in a coating with inhomogeneous microscale drug coverage on the surface, limiting the ability to deliver a consistent dose per unit surface area to surrounding tissue.

Example 4

This Example Describes the Preparation of a Kinetically Unstable Emulsion Comprising a Non-Aqueous Fluoropolymer Solution and a Water-Soluble Drug Solution and the Inherent Difficulty Associated with Using Said Un-Stable Emulsion to Coat a Substrate Solution D was prepared as per Example 2. A second solution (referred herein as Solution A) was formed by dissolving 1.0 g dexamethasone sodium phosphate (DSP) (Spectrum, Gardena, Calif.) solution in 3.0 g water.

A kinetically un-stable emulsion (referred herein Unstable Emulsion D) was formed by adding 1.11 g Solution A to 100 g Solution D while stirring. Immediate phase separation was seen to occur despite constant stirring. Unstable Emulsion D contained approximately 98.81% FC77, 0.82% water, 0.27% DSP, and 0.10% PATT-D (g per g total un-stable emulsion). The theoretical solids loading (g per g total solids) of DSP and PATT-D in this Unstable Emulsion D was 73% and 27%, respectively. Unstable Emulsion D was continuously stirred for approximately 1 h using a conventional stir plate. When stirring was halted, the aqueous phase was seen to immediately (within 30 seconds) partition to the top of the storage vessel, as depicted in FIGS. 4(c) and 5(c)(i) demonstrating the inherent kinetic instability of the suspension (aqueous phase partitioning represented schematically in FIG. 5(c)(ii)).

A film of expanded polytetrafluoroethylene (WL Gore & Associates, Inc.) was fixed to a flat surface. Unstable Emulsion D was pumped through a 30 psig, atomizing spray, nozzle (Spraying Systems Co., Laguna Hills, Calif.) at 10 ml/min for approximately 10 min. Five circular film samples (DE1 through DE5; 15.5 mm in diameter) were cut from the coated film.

Samples DE1 through DE 3 (DE1-3) were analyzed for DSP loading according to the following steps. First, all samples were weighed. To estimate the total coating mass applied, the mass of samples DE1-3 was compared to the average mass of uncoated film samples of equal size. The average coating mass of samples DE1-3 was 1001.07±89.54 μg/$cm^2$.

Samples DE1-3 were then placed in separate vials containing 3 ml phosphate buffered saline (PBS) (0.15M NaCl, pH 7.4, Invitrogen Corporation Carlsbad, Calif.). The samples remained in the PBS for 72 hrs. After this time, DSP in the PBS supernatant was analyzed by measuring UV absorption at 242 nm. Specifically, standards of known amounts of DSP in PBS were prepared and analyzed by UV spectroscopy. A linear standard curve of absorbance at 242 nm vs. DSP concentration was then generated. Absorbance within the supernatant of each sample was then compared to the standard curve in order to calculate DSP concentration. Average DSP loading in the samples was 2.12±0.20 μg/$cm^2$ as depicted in FIG. 6(*a*) (0.21%, FIG. 6(*b*)), which is far below the theoretical 73% loading.

Scanning electron microscopy (SEM) was used to image a sample (Sample DE5) of coated film (FIG. 7(*d*)). As shown of FIG. 7*d*, a uniform polymer layer was seen to coat the film, but no drug could be seen.

As these results indicate, kinetically unstable emulsions with a fluoropolymer and a fluorinated solvent combined with an aqueous DSP solution do not form kinetically stable solutions suitable for coating a substrate with a therapeutic agent.

Example 5

This Example Describes the Preparation of a Kinetically Stable Emulsion Comprising a Non-Aqueous Fluorinated Copolymer Solution (Class III Solvent) and a Water-Soluble Drug Solution and the Utility of Using Said Stable Emulsion to Coat a Substrate Solution V was prepared according to Example 3. Solution A was prepared according to Example 4.

A stable emulsion (referred herein Stable Emulsion V) was formed by adding 1.11 g Solution A to 100 g Solution V while stirring. The resulting emulsion was opaque in appearance, but did not undergo phase separation. Stable Emulsion V contained approximately 98.81% acetone, 0.82% water, 0.27% DSP, and 0.10% TFE-VAc (g per g total emulsion). The theoretical solids loadings (g per g total solids) of DSP and TFE-VAc in this stable emulsion were 73% and 27%, respectively. Stable Emulsion V was stirred for approximately 1 hr using a conventional stir plate. When stirring was halted, surprisingly no phase separation or DSP precipitation was seen to occur for a period of at least 15 minutes, as depicted in FIGS. 4*d* and 5(*d*)(*i*), and as such is determined to be kinetically stable (no phase separation or DSP precipitation represented schematically in FIG. 5(*d*)(*ii*)).

A film of expanded polytetrafluoroethylene (WL Gore & Associates, Inc.) was fixed to a flat surface. Stable Emulsion V was pumped through a 30 psig, atomizing spray, nozzle (Spraying Systems Co., Laguna Hills, Calif.) at 10 ml/min for approximately 10 min. Five film samples (VE1 through VE5; 15.5 mm in diameter) were cut from the coated film.

Samples VE1 through VE3 (VE1-3) were analyzed for DSP loading according to the following steps. First, all samples were weighed. To estimate the total coating mass applied, the mass of samples VE1-3 was compared to the average mass of uncoated film samples of equal size. The average coating mass of samples VE1-3 was 839.00±56.10 µg/cm$^2$.

Figure 6B:
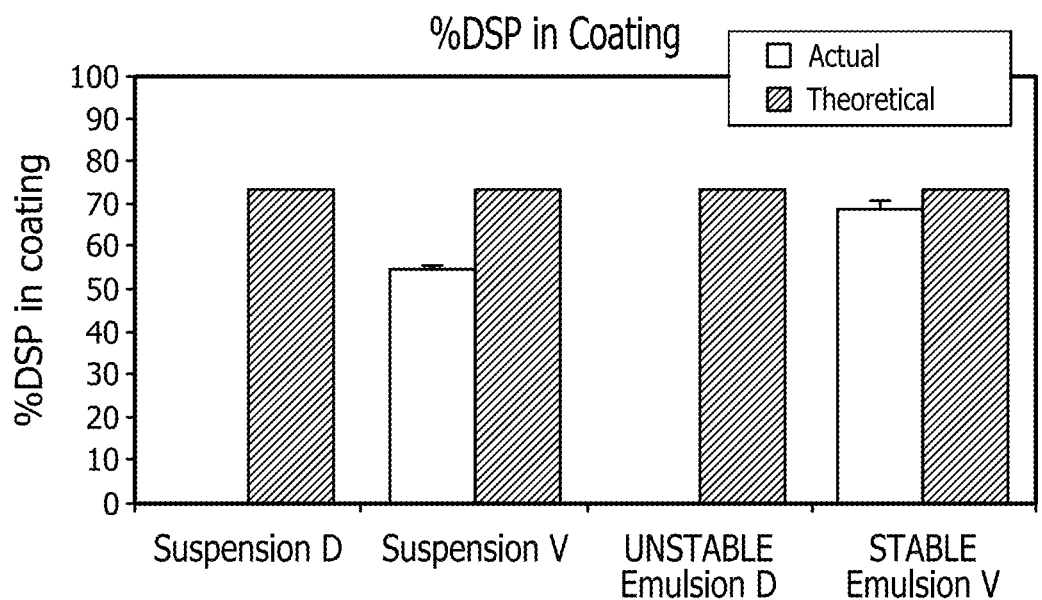
FIG. 6(b) depicts percent dexamethasone sodium phosphate (DSP) in film samples coated with Suspension D, Suspension V, Kinetically Unstable Emulsion D, or Kinetically Stable Emulsion V, as described in the Examples.

Then, samples VE1-3 were then placed in separate vials containing 3.0 ml phosphate buffered saline (PBS) (0.15M NaCl, pH 7.4, Invitrogen Corporation Carlsbad, Calif.). The samples remained in the PBS for 72 hrs. After this time, DSP in the PBS supernatant was analyzed by measuring UV absorption at 242 nm. Specifically, standards of known amounts of DSP in PBS were prepared and analyzed by UV spectroscopy. A linear standard curve of absorbance at 242 nm vs. DSP concentration was then generated. Absorbance within the supernatant of each sample was then compared to the standard curve in order to calculate DSP concentration. Average DSP loading in the samples was 578.27±18.19 µg/cm$^2$ (FIG. 6(a)). The percent DSP in this final coating (69%; FIG. 6(b)) was seen to approximate the ratio of DSP to total solids in Stable Emulsion V (73%), indicating the uniformity of this coating method.

Figure 7E:
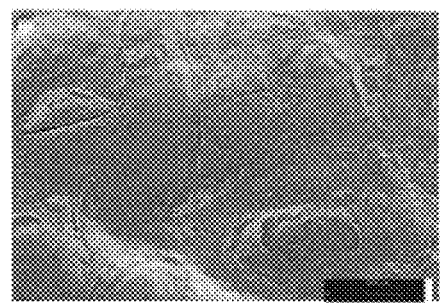

Scanning electron microscopy (SEM) was used to image a sample (Sample VE5) of coated film (FIG. 7(e)). As shown of FIG. 7(e), the film had a homogeneous appearance. A uniform polymer layer with intermixed DSP particles on a microscale could be seen on the film. The homogenous microscale distribution of the drug phase is superior to the drug phase separation or precipitation as seen in the prior art.

As these results indicate, a kinetically stable emulsion of a fluoropolymer dissolved in an organic Class III Solvent with a water-soluble drug is of utility. The theoretical and actual DSP loading were consistent for this system, and the homogeneous microscale drug coverage on the surface is highly desirable for reasons explained herein.

Example 6

This Example Describes the Preparation of a Kinetically Stable Emulsion Comprising a Non-Aqueous Fluorinated Copolymer Solution (Class III Solvent) and an Aqueous Solution of the Angiographic Contrast Agent Iohexol A clear, transparent solution (referred herein as Solution V5) was prepared by dissolving 1.00 g poly(tetrafluoroethylene-co-vinyl acetate) (TFE-VAc) (as synthesized according to Example 1, #100-0) in 1000 g acetone (Sigma Aldrich, St. Louis, Mo.). A second solution (referred herein as Solution I5) was prepared by dissolving 1.04 g iohexol (Chemos Gmbh, Regenstauf, Germany) in 5 g water. Solution I5 was clear and translucent in appearance.

A kinetically stable emulsion (referred herein Stable Emulsion V5) was formed by adding approximately 2.0 g Solution 15 to 185.0 g Solution V5 while stirring. Kinetically Stable Emulsion V5 was opaque in appearance. When stirring was halted, no phase separation or precipitation was seen to occur for a period of at least 15 minutes.

A film of expanded polytetrafluoroethylene (WL Gore & Associates, Inc.) was fixed to a flat surface. Stable Emulsion V5 was pumped through a 30 psig, atomizing spray, nozzle (Spraying Systems Co., Laguna Hills, Calif.) at 10 ml/min for approximately 20 min. Three coated film samples (15.5 mm in diameter) were cut from the film and analyzed for iohexol loading.

The coated samples were first weighed. The mass of each coated sample was compared to the average mass of uncoated film samples of equal size to estimate the total coating mass applied. The average coating mass was 899.17±122.01 µg/cm$^2$.

The coated samples were then placed in separate vials containing 3 ml phosphate buffered saline (PBS) (0.15M NaCl, pH 7.4, Invitrogen Corporation Carlsbad, Calif.). The samples remained in the PBS for 120 hrs to allow for iohexol extraction. After this time, iohexol in the PBS supernatant was analyzed by measuring UV absorption at 245 nm. Standards of known amounts of iohexol in PBS were also prepared and analyzed by UV spectroscopy. A linear standard curve of absorbance at 245 nm vs. iohexol concentration was then generated. This curve was then used to estimate the iohexol concentration within the supernatant of each coated sample.

Average iohexol loading in the coated samples was 495.81±46.55 µg/cm$^2$. The percent iohexol in this final coating (55%) was seen to approximate the ratio of iohexol to total solids in Stable Emulsion V5 (65%), indicating the uniformity of this coating method.

As these results indicate, a kinetically stable emulsion of a fluoropolymer dissolved in an organic Class III Solvent with an water-soluble agent is of utility. The theoretical and actual loadings were consistent for this system.

Example 7

This Example Describes the Preparation of a Kinetically Stable Emulsion Comprising a Non-Aqueous Fluorinated Copolymer Solution (Class III Solvent) and an Aqueous, Colloidal Gold Solution A clear, transparent solution (referred herein as Solution V6) was prepared by dissolving 2.68 g poly(tetrafluoroethylene-co-vinyl acetate) (TFE-VAc) (as synthesized according to Example 1, #100-0) in 1000.0 g acetone (Sigma Aldrich, St. Louis, Mo.). A second solution (referred herein as Solution G6) was obtained from Sigma Aldrich (St. Louis, Mo.). Solution G6 contained approximately 0.01% chloroauric acid ($HAuCl_4$; by weight). Solution G6 was translucent in appearance with a reddish hue.

A kinetically stable emulsion (referred herein Stable Emulsion V6) was formed by adding approximately 26.0 g Solution G6 to 95 g Solution V6 while stirring. Stable Emulsion V6 was translucent in appearance with a purple hue. When stirring was halted, no phase separation or precipitation was seen to occur for a period of at least 30 minutes, and thus was kinetically stable.

A circular film (approximately 2.0 inches in diameter) of expanded polytetrafluoroethylene (WL Gore & Associates, Inc.) was fixed to a flat surface. The ePTFE film was spray-coated with Stable Emulsion V6 using a Badger airbrush (Model 350, Badger Air Brush Co., Franklin Park, Ill.) set at 15 psig air pressure. Spray coating was conducted for 2-3 minutes. Then, the coating was allowed to air dry before the film was once again spray-coated. This iterative process was use to spray the film with approximately 121.0 g Stable Emulsion V6. No clogging of the air brush or other malfunctioning was observed.

As these results indicate, a kinetically stable emulsion comprising a non-aqueous fluorinated copolymer solution (Class III solvent) and an aqueous, colloidal gold solution has been successfully utilized to coat a substrate.

Example 8

Synthesis of a Copolymer Comprising Tetrafluoroethylene and Functional Groups Comprising Alcohol (TFE-VOH)

The vinyl acetate groups of copolymer #100-0 of Example 1 were hydrolyzed to vinyl alcohol as follows. To a 50 ml round bottle flask were added 0.5 g of copolymer

100-0 (predissolved in 10 ml methanol) and 0.46 g NaOH (predissolved in 2 ml DI water). The mixture was stirred and heated to 60° C. for 5 hrs. The reaction mixture was then acidified to pH 4, precipitated in DI water, dissolved in methanol, and again precipitated in DI water. The resulting product was a copolymer of TFE-VOH.

Example 9

Preparation of Emulsions Comprising Non-Aqueous Fluoropolymer Solution and Aqueous Drug Solution Emulsions were prepared using the following general scheme. A first solution of each copolymer from Example 1 was prepared by dissolving 0.1 g of the TFE-VAc copolymers in 99.9 g acetone (Sigma Aldrich, St. Louis, Mo.) to produce a 0.1% wt polymer solution. A second solution was formed by dissolving 5.0 g dexamethasone sodium phosphate (DSP) (Spectrum, Gardena, Calif.) in 15.0 g water to produce a 25% wt drug solution.

Emulsions were formed by adding drop wise 0.52 g of the drug solution to 50 g of each polymer solution with vigorous stirring. The resulting emulsions were opaque in appearance. The resulting emulsions contained approximately 98.83% acetone, 0.80% water, 0.27% DSP, and 0.10% TFE-VAc (g per g total emulsion).

Example 10

Kinetic Stability of Emulsions Comprising Non-Aqueous Fluoropolymer Solution and Aqueous Drug Solution To examine kinetic stability of the emulsions of Example 9, each emulsion was allowed to stand on a bench top for four hours, and then visually inspected. All of the emulsions showed an absence of visible precipitation or gelation, indicating kinetic stability of the emulsion at this time frame. As an additional test of stability, each emulsion was sprayed onto an aluminum test substrate using a Badger airbrush (Model 350, Badger Air Brush Co., Franklin Park, Ill.) at a pressure of 20 psi. As a further indication of emulsion stability, the tip did not clog during the spray test for any of the emulsions.

To examine long-term kinetic stability of the emulsions of Example 9, they were allowed to stand on a bench top for 7 days. After 1 day, all of the emulsions showed an absence of visible precipitation or gelation, indicating kinetic stability of the emulsion at this time frame. After 7 days, emulsions comprising copolymers #100-1 and #100-2 had gelled, whereas emulsions comprising copolymers #100-0, #100-3 and #100-4 remained stable. All emulsions were successfully sprayed onto an aluminum test substrate at a pressure of 20 psi without clogging or otherwise blocking the spray tip, including emulsions comprising #100-1 and #100-2.

As these results indicate, all emulsions of Example 9 are kinetically stable emulsions.

Example 11

Maximum Water Content in Fluoropolymer Emulsions to Reach Opacity Point

The copolymers of Example 1 were dissolved in acetone, and then water was added with vigorous stirring to form an emulsion. The maximum water that could be added to the emulsion was determined by the following procedure. A polymer solution was prepared by dissolving 1.0 g of the copolymers of Example 1 in 99.0 g of acetone to make a 1% wt solution. 2.0 g of this polymer solution was added to a 20 ml vial, and deionized water was added dropwise with vigorous stirring to form an emulsion. The water was continued to be added dropwise until the emulsion became opaque. This amount of water was determined to be the maximum water content that the clear kinetically stable copolymer emulsion could tolerate, and is termed the opacity point. The results show that emulsions made with copolymer 100-3, which has the highest vinyl acetate content and molecular weight, tolerated more water than emulsions made with the other copolymers, and hence, has a higher opacity point.

TABLE 4

Maximum water content of TFE-VAc emulsions

| | Copolymer # | | | |
|---|---|---|---|---|
| | 100-1 | 100-2 | 100-3 | 100-4 |
| Water wt % | 23.0% | 22.1% | 27.6% | 22.0% |

Example 12

Preparation of Embolics Comprising TFE-VOH Fluoropolymer Emulsions

Embolics comprising TFE-VOH emulsions were examined in vitro using the following general procedure. Organic solvent, including DMSO, triethylene glycol (TEG, Fluka), polyethylene glycol 200 (PEG200, Spectrum), and propylene glycol (PG, Aldrich) was mixed with water at varying wt % to form a solvent/water mixture. TFE-VOH (synthesized according to Example 8) was weighed into a glass vial, and a known mass of solvent/water mixture was added to the vial. The vial was heated at 80° C. with gentle tumbling for two hrs to emulsify the copolymer and then cooled to room temperature. The emulsion was extruded via 22 ga syringe needle into Petri dishes filled with phosphate buffered saline (PBS), whereupon the solvent/water mixture diffused from the emulsion. The ability of the emulsion to form a coherent coagulated bolus at the tip of the needle, without dispersing or particulating, was assessed. For comparison, solutions of copolymer dissolved in solvent only (no water) were similarly prepared and assessed.

TABLE 5

Bolus Formation Comparison Chart

| Embolic type | Solvent | water % | Copolymer Wt % | Form bolus? |
|---|---|---|---|---|
| Solution | DMSO | | 5% | no |
| Solution | DMSO | | 8% | yes |
| Solution | DMSO | | 10% | yes |
| Solution | TEG | | 5% | yes |
| Solution | TEG | | 8% | yes |
| Solution | PEG200 | | 5% | no |
| Emulsion | DMSO/water | 40% | 6.5% | yes |
| Emulsion | DMSO/water | 45% | 10% | no |
| Emulsion | DMSO/water | 45% | 15% | yes |
| Emulsion | DMSO/water | 40% | 10% | no |
| Emulsion | DMSO/water | 40% | 15% | yes |
| Emulsion | TEG/water | 45% | 6.5% | no |
| Emulsion | TEG/water | 45% | 8% | no |
| Emulsion | TEG/water | 40% | 8% | yes |
| Emulsion | PEG200/water | 40% | 8% | yes |
| Emulsion | PG/water | 40% | 8% | yes |
| Emulsion | PG/water | 30% | 6.5% | yes |

Example 13

Maximum Water Content in TFE-VOH Embolic Emulsions

TFE-VOH (synthesized according to Example 8) was dissolved in DMSO to form a 10 wt % solution, and then water was added drop wise with vigorous stirring to form an emulsion. The maximum water that could be added drop wise to the emulsion until the emulsion became opaque was determined to be 47% water. This result shows, compared to Example 11 that the TFE-VOH copolymer emulsion could tolerate significantly more water compared to TFE-VAc copolymers emulsions before reaching the opacity point.

Example 14

Preparation of Emulsions Comprising a Non-Aqueous Fluorinated Copolymer Solution and an Aqueous Drug Solution Embolics comprising emulsions comprising TFE-VOH were examined in vitro using the following general procedure. An aqueous drug solution was prepared by dissolving a water soluble phase contrast agent, iohexol USP (Omnipaque, GE Healthcare), into 60 wt % DMSO/40 wt % water, at concentrations of 140 and 240 mg l/ml. The TFE-VOH copolymer (synthesized according to Example 8) was added at concentrations of 6, 8, and 10 wt %, and heated to 80° C. with gentle tumbling for two hrs to form emulsions. The emulsions were extruded via a 2.5 Fr catheter (Rebar, EV3) into a Petri dish filled with PBS. All the emulsions formed a soft skin upon contact with the PBS, and formed a coherent intact bolus with no dispersion or particulation. All boluses were radiopaque and visible under single-shot exposure fluoroscopy at 20 min post-extrusion; after 24 hrs, they were no longer radiopaque under single-shot exposure fluoroscopy, indicating diffusion of the phase contrast agent from the bolus.

Example 15

Kinetic Stability of Emulsions Comprising TFE-VOH Fluoropolymer

Selected emulsions of Example 12 and Example 14 were allowed to sit undisturbed on a bench top. As an indication of kinetic stability, they were examined periodically for transparency and for absence of precipitation, gelation, phase separation, or opacity. The following emulsions, with and without iohexol phase contrast agent, were transparent and were without precipitation, gelation, phase separation, or opacity for at least 1 year, indicating long-term kinetic stability.

TABLE 6

TFE-VOH emulsions with 1 yr kinetic stability.

| Solvent | water % | Copolymer wt % | iohexol mg l/ml |
|---|---|---|---|
| DMSO/water | 40% | 8% | * |
| PG/water | 40% | 8% | * |
| PEG150/water | 40% | 8% | * |
| TEG/water | 40% | 8% | * |
| DMSO/water | 40% | 6% | 140 |
| DMSO/water | 40% | 8% | 140 |
| DMSO/water | 40% | 10% | 140 |
| DMSO/water | 40% | 8% | 240 |

* Iohexol not added to emulsion

Example 16

Embolization of an Ovine Kidney Using an Emulsion Comprising Non-Aqueous Fluoropolymer Solution and Aqueous Drug Solution An emulsion of TFE-VOH was examined in vivo for its ability to embolize an organ. A female domestic sheep was anesthetized. A renal artery was accessed via a femoral artery using microcatheter techniques. A 2.5 Fr microcatheter (Rebar, EV3) was primed with a solution of 60/40% DMSO/water, and then inserted into the renal artery. Approximately 1 ml of an emulsion comprising 6 wt % TFE-VOH (synthesized according to Example 8) and 140 mg l/ml iohexol (Omnipaque, GE Healthcare), in 60/40% DMSO/water, was injected into the renal artery under angiography visualization.

Figure 8B:
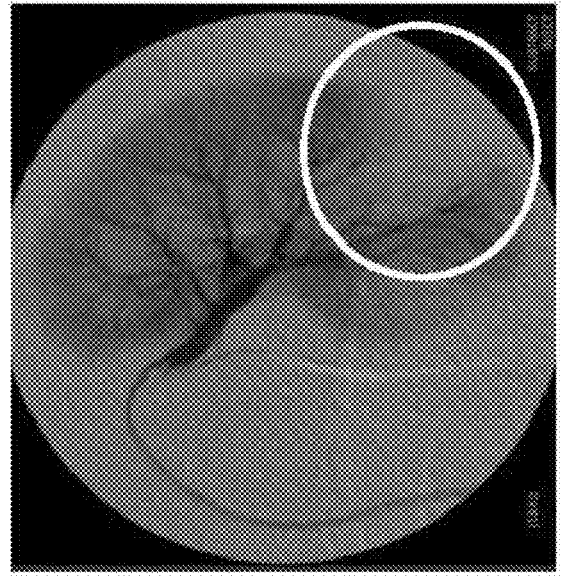
FIGS. 8(a) and 8(b) depict an ovine kidney pre- and post-embolization, respectively.
Figure 8A:
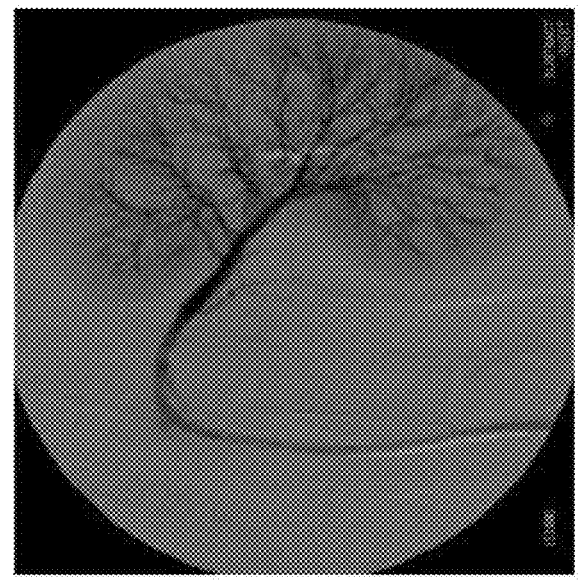

Angiography demonstrated distal penetration of the emulsion with no evidence of vasospasm. The microcatheter was left in vivo for 2 min to allow the extruded emulsion to form a skin and harden into a coherent embolic bolus. After the 2 min dwell time, the microcatheter was withdrawn, there was no evidence the bolus had adhered to the catheter tip or had everted the renal artery. Furthermore, there was no evidence the DMSO/water solution had damaged the microcatheter or other surgical equipment. Contrast angiography confirmed embolization of the kidney. FIGS. 8(a) and 8(b) depict an ovine kidney pre- and post-embolization, respectively.

Example 17

Embolization of an Ovine Kidney Using an Emulsion Comprising Non-Aqueous Fluoropolymer Solution and Aqueous Drug Solution An emulsion of TFE-VOH was examined in vivo for its ability to embolize an artery. A female domestic sheep was anesthetized. A renal artery was accessed via a femoral artery using microcatheter techniques. A 2.5 Fr microcatheter (Rebar, EV3) was primed with a solution of 60/40% DMSO/water, and then inserted into the renal artery. Approximately 1 ml of an emulsion comprising 8 wt % TFE-VOH (synthesized according to Example 8) and 240 mg l/ml iohexol, dissolved in 60/40% DMSO/water, was injected into the renal artery under angiography visualization.

Angiography demonstrated distal penetration of the emulsion with no evidence of vasospasm. The microcatheter was left in vivo for 2 minutes to allow the extruded emulsion to form a skin and harden into a coherent embolic bolus. After the 2 min dwell time, the microcatheter was withdrawn, there was no evidence the bolus had adhered to the catheter tip or had everted the renal artery. Furthermore, there was no evidence the DMSO/water solution had damaged the microcatheter or other surgical equipment. Contrast angiography confirmed embolization of the kidney.

Example 18

Embolization of a Porcine Kidney Using an Emulsion Comprising Non-Aqueous Fluoropolymer Solution and Aqueous Drug Solution An emulsion of TFE-VOH was examined in vivo for its ability to embolize an artery. A female domestic swine was anesthetized. A renal artery was accessed via a femoral artery using microcatheter techniques. A 2.8 Fr microcatheter (Rebar, EV3) was primed with a solution of 60/40% PG/water, then inserted into the renal artery. Approximately 1 ml of an emulsion comprising 8 wt % TFE-VOH (synthesized according to Example 8) and 140 mg l/ml iohexol, dissolved in 60/40% PG/water, was injected into the renal artery under angiography visualization. Angiography demonstrated distal penetration of the emulsion with no evidence of vasospasm. The microcatheter was left in vivo for 2 min to allow the extruded emulsion to form a skin and harden into a coherent embolic bolus. After the 2 min dwell time, the microcatheter was withdrawn, there was no evidence the bolus had adhered to the catheter tip or had everted the renal artery. Furthermore, there was no evidence the PG/water solution had damaged the microcatheter or other surgical equipment. Contrast angiography confirmed embolization of the kidney. FIGS. 9(a) and 9(b) depict a porcine kidney pre- and post-embolization, respectively.

Example 19

Embolization of an Ovine Hamstring Using an Emulsion Comprising Non-Aqueous Fluoropolymer Solution and Aqueous Drug Solution An emulsion of TFE-VOH was examined in vivo for its ability to embolize a muscle. A female domestic sheep was anesthetized. Approximately 1 ml of an emulsion of Example 17, was injected into the hamstring via an 18 ga needle under angiography visualization. Angiography demonstrated distal penetration of the emulsion with no evidence of muscle spasm. Contrast angiography confirmed embolization of the muscle.

Example 20

Injection of an Emulsion Comprising Non-Aqueous Fluoropolymer Solution and Aqueous Drug Solution into a Casing An emulsion of TFE-VOH was examined ex situ for its ability to be injected into a casing for occluding a body lumen or space.

A casing was made from an ePTFE film tube. The ePTFE film tube was made from 12 mm wide ePTFE film by helically wrapping a 14 mm diameter SST mandrel in a bias-ply fashion at an angle of approx 20°. The mandrel and film tube were then subjected to a heat treatment in a Grieve Industrial Oven model NT-1000 of 370° C. for 15 minutes and allowed to cool. The film tube was then removed from the mandrel and stretched longitudinally until the diameter was reduced to approx 3 mm. A knot was tied at one end of the film tube, and excess material trimmed with scissors at a length of approx 14 mm from the knot. The opposite end of the film tube was attached to an adhesive dispensing needle (Nordson EFD, East Providence, R.I.; part number 7018068) with cyanoacrylate adhesive and overwrap of the same ePTFE film as above. The resultant casing comprised an approx 3 mm diameter ePTFE film-tube, sealed at one end and attached to a dispensing needle at the opposite end, and was distensible up to about 12 mm in diameter via injection of fluid medium via the dispensing needle into the film tube.

Approximately 2 ml of an emulsion made according to Example 18, was injected into the casing via the dispensing needle. The emulsion readily injected through the dispensing needle and partially inflated the casing. The casing was briefly immersed in methanol to wet out the ePTFE, then transferred immediately into a beaker filled with deionized water. Propylene glycol from the emulsion was observed to diffuse across the ePTFE film tube into the deionized water. Approximately 1 ml of deionized water was subsequently injected into the casing while it was immersed in the beaker. The emulsion was observed to form a spongy, compliant mass within the casing within 10 minutes, with no precipitation or particulation observed crossing the ePTFE film tube or otherwise escaping the casing. FIG. 10 depicts the prepared emulsion injected into an occlusive casing.

Example 21

Characterization of the Drug Distribution in a Coated Film Formed from an Emulsion of a Water-Soluble Agent Dispersed in a Non-Aqueous Fluoropolymer Solution Drug coated films were prepared in accordance with Examples 2-5 and respectively referred to as DS, VS, DE, and VE. Confocal Raman spectroscopy (LabRAM ARAMIS; Horiba Scientific; Kyoto, Japan) was utilized on the films to obtain special maps of the ePTFE substrate, DSP content, and copolymer used in the coating. This mapping data can infer coating consistency of coverage, and extent of drug content uniformity. Wavelengths for the copolymer and DSP were 631.2 and 532.0 $cm^{-1}$ respectively.

Sample DS, which comprises a kinetically unstable suspension of a fluoropolymer dissolved in a fluorinated solvent with a water-soluble drug, showed essentially no coating and no drug coverage using confocal Raman spectroscopy.

Sample VS, which comprises a kinetically unstable suspension of a fluoropolymer dissolved in an organic Class 3 Solvent with a water-soluble drug, showed inconsistent drug coverage, as any drug present was observed as small discrete aggregates using confocal Raman spectroscopy.

Sample DE, which comprises a kinetically unstable emulsion of a fluoropolymer and a fluorinated solvent combined with an aqueous DSP solution, showed essentially no drug using confocal Raman spectroscopy Sample VE, which comprises a kinetically stable emulsion of a fluoropolymer dissolved in an organic Class III Solvent with a water-soluble drug, showed a high degree of consistent coverage with a uniform distribution of drug at a high drug content, using confocal Raman spectroscopy.

Example 22

Syntheses of a copolymer comprising tetrafluoroethylene and functional groups comprising amine (TFE-VOH-AcAm)

The amine-containing fluoropolymer, poly(tetrafluoroethylene-co-vinyl alcohol-co-vinyl[aminobutyraldehyde acetal])(TFE-VOH-AcAm), was prepared using the following conditions.

The copolymer of Example 8 was dissolved in methanol at 2.5% w/v. To 50 g of this solution was added 33 ml of DI water with vortexing to produce a homogeneous solution. To this solution was added 0.153 g of aminobutyraldehyde dimethyl acetal (Aldrich), and 0.120 ml of a 37% HCl solution. The solution was reacted with stirring under nitrogen, 80° C., for 48 hrs. Sodium hydroxide from a 1M solution was added drop wise to a pH of about 9.0. The resulting TFE-VOH-AcAm copolymer was recovered by precipitation into copious DI water. The precipitate was filtered, redissolved into methanol, and reprecipitated into copious DI water for two more cycles. The final product was dried under vacuum at 60° C. for 3 hrs. FTIR and carbon NMR confirmed a polymer structure comprising tetrafluoroethylene and functional groups comprising amine linked to the polymer backbone via acetal groups.

Example 23

Preparation of Emulsions Comprising Non-Aqueous Fluoropolymer Solution and Aqueous Drug Solution An emulsion is prepared using the following general scheme. A first solution was prepared by dissolving 0.1 g of the TFE-VOH-AcAm copolymer from Example 22 in 99.9 g acetone to produce a 0.1% wt polymer solution. A second solution is formed by dissolving 5.0 g dexamethasone sodium phosphate (DSP) (Spectrum, Gardena, Calif.) in 15.0 g water to produce a 25% wt drug solution.

An emulsion is formed by adding dropwise 0.52 g of the drug solution to 50 g of the polymer solution with vigorous stirring. The resulting emulsions are opaque in appearance, but do not undergo phase separation. The resulting emulsions contain approximately 98.83% acetone, 0.80% water, 0.27% DSP, and 0.10% TFE-VOH-AcAm (g per g total emulsion). The emulsion is stirred for approximately 1 hr using a conventional stir plate. When stirring is halted, no phase separation or DSP precipitation is seen to occur for a period of at least 15 minutes, and as such is determined to be kinetically stable.

Example 24

M-DSC Study to Assess the Degree of Molecular Mixing

This Example describes the molecular mixing between a fluorinated copolymer and a water-soluble drug when coated onto a substrate, as measured by modulated differential scanning calorimetry (M-DSC).

M-DSC was used to examine the degree of molecular mixing between a fluorinated copolymer phase comprising TFE-VAc and a water-soluble drug phase comprising DSP, when applied onto a substrate.

M-DSC is capable of discriminating between thermodynamic and kinetic contributions to a polymer's thermal properties during an oscillating heating ramp (see for example, J D Menczel, "Differential Scanning Calorimetry (DSC)", in Thermal Analysis of Polymers: Fundamentals and Applications, J D Menczel (Ed.), Wiley, 2009, pp 168-208, incorporated herein by reference). The total heat flow is split into reversing (thermodynamic) and non-reversing (kinetic) heat flows. The reversing heat flow derives from the heat capacity of the sample; phenomena such as copolymer domain demixing/remixing, polymer chain unfolding/refolding, copolymer phase reorganization, and the like, contribute to an excess heat capacity measured as a reversing exothermic transition. These transitions are reversible events that respond to the oscillating heating ramp. Non-reversing heat flows are those events that do not respond to the oscillating heating ramp, including transitions such as melting measured as a non-reversing endothermic transition.

The presence or absence of molecular-scale interactions between the fluorinated copolymer phase and the water-soluble drug phase can be detected in the reversing and non-reversing heat flows. If the water-soluble drug phase is capable of mixing at a molecular scale with the fluorinated copolymer phase, it may plasticize the fluorinated copolymer's crystallinity, and/or may aid in compatibilizing the fluorinated and non-fluorinated segments of the polymer chain. Such events are detectible in the non-reversing endothermic transition and/or in the reversing exothermic transition, respectively.

Coated substrate "TFE-VAc coated" was prepared. Solution V of Example 3 was coated onto a film of expanded polytetrafluoroethylene (WL Gore & Associates, Inc.) following the procedure of Example 3 to form the coated substrate "TFE-VAc coated". The average coating mass of "TFE-VAc coated" was approximately 431 ug/cm2 after drying.

Coated substrate "Suspension V" was prepared according to Example 3.

Coated substrate "STABLE Solution V" was prepared. To 100 g of Solution V from Example 3 was added 1.0 g dexamethasone (Spectrum), to provide a ratio of 9% TFE-VAc polymer:91% dexamethasone. Acetone is a solvent for dexamethasone, and the dexamethasone was seen to dissolve completely in Solution V. The solution was sprayed onto a film of expanded polytetrafluoroethylene (WL Gore & Associates, Inc.) following the procedure of Example 3 to form the coated substrate "STABLE Solution V". The average coating mass of "STABLE Solution V" was approximately 2720 ug/cm2 after drying.

Coated substrate "STABLE Emulsion V" was prepared according to Example 5.

For the M-DSC analysis, 5-10 mg samples of each coated substrate were examined using M-DSC Model # Q2000 (TA Instruments, New Castle, Del.), from −20° C. to 100° C., using a heating ramp of 5° C./min, with an oscillation rate of +/−0.5° C. every 40 sec. After heating, samples were returned to room temperature for at least 2 hrs, and run a second time.

TFE-VAc (as synthesized according to Example 1, #100-0, "TFE-VAc resin") showed a prominent reversing exotherm (excess heat capacity) overlapped with a prominent non-reversing endotherm (melting transition) in the temperature range of about 45-55° C. Expanded polytetrafluoroethylene, PATT-D, DSP, and dexamethasone do not show reversing or non-reversing transitions in this temperature range; thus, any transition observed in the range of about 45-55° C. was attributable solely to the TFE-VAc copolymer component.

Figure 12:
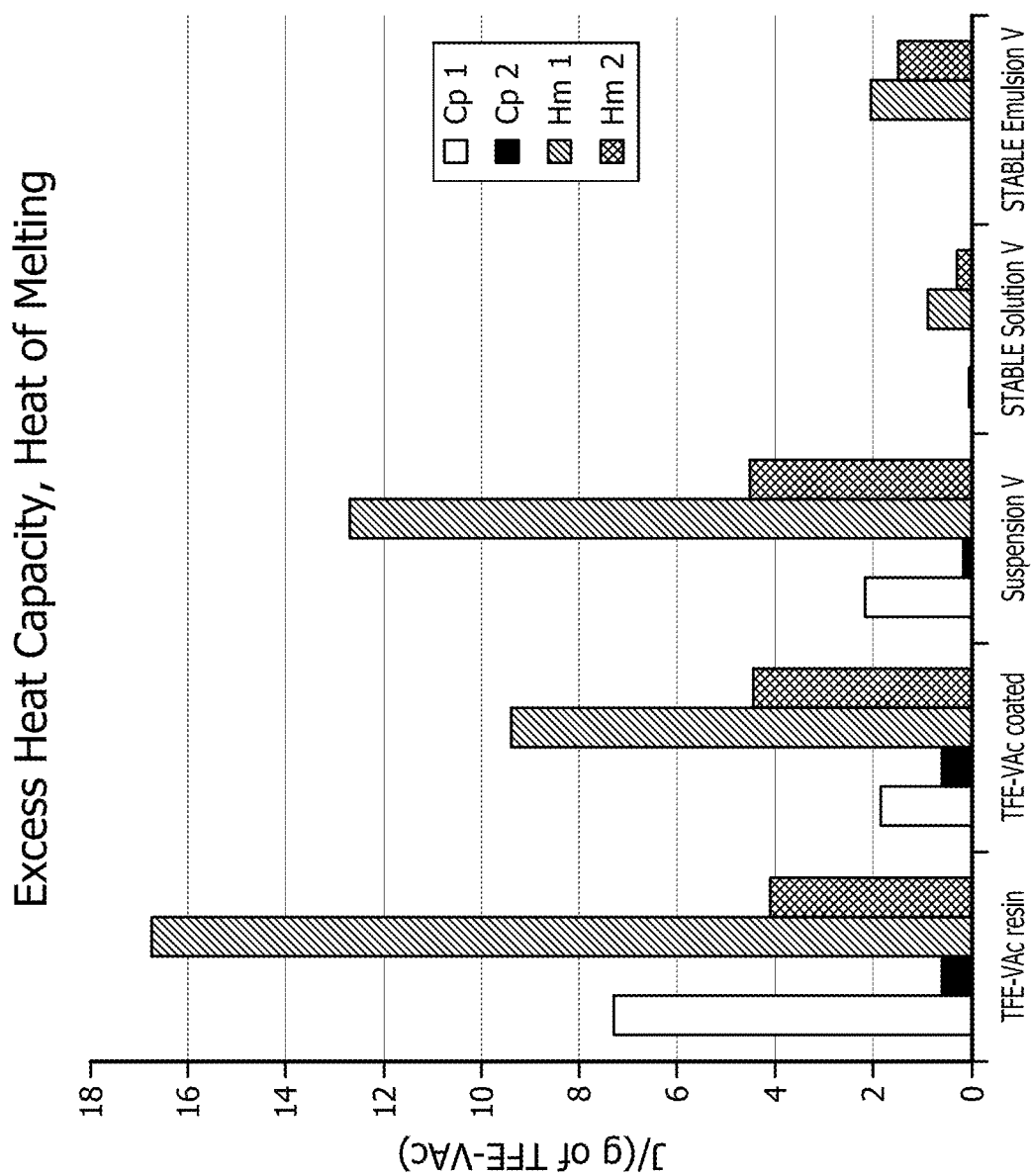
FIG. 12 shows the magnitudes of the reversing excess heat capacity and non-reversing melt transitions as described in Example 24.

FIG. 12 shows the magnitude of the first and second reversing excess heat capacity (Cp1 and Cp2) and the first and second non-reversing melt (Hm1 and Hm2) transitions from the first and second heating runs for the tested samples, in the range of about 45-55° C., normalized to the mass of TFE-VAc present in each sample.

When TFE-VAc was dissolved in solvent and applied onto a substrate ("TFE-VAc coated"), there was a reduction in the Cp1 (about 75%) and Hm1 (about 45%) compared to the base resin ("TFE-VAc resin"). This result indicated some loss of crystallinity and some loss of excess heat capacity of the TFE-VAc attributable to the dissolution, spraying, and drying processes during coating. However, the second heating run (Cp2 and Hm2) of the coated substrate was nearly identical to the base resin, indicating that the coating process did not affect the inherent thermal properties of TFE-VAc.

When a suspension of water-soluble DSP in a non-aqueous TFE-VAc solution was applied onto a substrate ("Suspension V"), the first and second Cp and Hm were nearly identical to the substrate comprising only TFE-VAc ("TFE-VAc coated"). This indicated the DSP phase did not mix on the molecular scale to any appreciable extent with the TFE-VAc phase and remained phase separated.

When a solution of solvent-soluble dexamethasone in a non-aqueous TFE-VAc solution was applied onto a substrate ("STABLE Solution V"), there was a large reduction in the Hm1 and Hm2 (about 90%) and a disappearance of Cp1 and Cp2, when compared to "TFE-VAc coated" or to "Suspension V". These reductions indicated mixing occurred on the molecular scale between dexamethasone phase and TFE-VAc phase, reducing the crystallinity of the TFE-VAc phase and increasing the segment compatibilization of the TFE-VAc phase.

When a kinetically stable emulsion of water-soluble DSP in water and non-aqueous TFE-VAc was applied onto a substrate ("STABLE Emulsion V"), it also showed a large reduction in Hm1 and Hm2 (about 80% and about 70%, respectively) and a disappearance of Cp1 and Cp2, when compared to "TFE-VAc coated" or to "Suspension V". Again, these reductions indicated mixing on a molecular scale occurred between DSP phase and TFE-VAc phase, reducing the crystallinity and increasing the segment compatibilization of the TFE-VAc phase. This is a surprising and unexpected result, as one of ordinary skill in the art would predict DSP and TFE-VAc would be incapable of mixing at a molecular level, as illustrated by "Suspension V". Without wishing to be bound by any particular theory, it is believed that the emulsion aids in the mixing at a molecular scale of the DSP phase with the TFE-VAc phase, a phenomenon that can not be attained using a suspension of DSP in TFE-VAc, regardless of how small or finely suspended the DSP particles may be.

Numerous characteristics and advantages of the present disclosure have been set forth in the preceding description, including preferred and alternate embodiments together with details of the structure and function of the disclosure. The disclosure is intended as illustrative only and as such is not intended to be exhaustive. It will be evident to those skilled in the art that various modifications can be made, especially in matters of structure, materials, elements, components, shape, size and arrangement of parts within the principals of the disclosure, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present disclosure is further directed to embodiments having different combinations of the features described above and claimed below. As such, the disclosure is also directed to other embodiments having any other possible combination of the dependent features claimed below.

1. A water in solvent emulsion comprising: a tetrafluoroethylene copolymer dissolved in a water miscible organic solvent; and a water soluble agent dissolved in water, wherein an opacity point for the emulsion is greater than 5% water and less than 60% by weight.

2. The water in solvent emulsion of claim 1, wherein said tetrafluoroethylene copolymer comprises a functional group selected from a group consisting of acetate, alcohol, amine, and amide.

3. The water in solvent emulsion of claim 2, wherein said tetrafluoroethylene copolymer is poly(tetrafluoroethylene-co-vinyl acetate).

4. The water in solvent emulsion of claim 2, wherein said tetrafluoroethylene copolymer is poly(tetrafluoroethylene-co-vinyl alcohol).

5. The water in solvent emulsion of claim 2, wherein said tetrafluoroethylene copolymer is poly(tetrafluoroethylene-co-vinyl alcohol-co-vinyl[aminobutyraldehyde acetal]).

6. The water in solvent emulsion of claim 2, wherein said water soluble agent is a therapeutic agent.

7. The water in solvent emulsion of claim 6, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel, sirolimus, cytostatic agents; cell proliferation affectors; vasodilating agents; cilostazol; carvedilol; antibiotics; and combinations thereof.

8. The water in solvent emulsion of claim 1, wherein said water soluble agent is an inclusion complex consisting of a hydrophilic complexing agent and a hydrophobic therapeutic agent.

9. The water in solvent emulsion of claim 8, wherein the inclusion complex consists of a cyclodextrin molecule and a hydrophobic therapeutic agent.

10. The water in solvent emulsion of claim 1, wherein said emulsion is applied onto a substrate.

11. The water in solvent emulsion of claim 10, wherein said emulsion is applied to said substrate using a single applicator comprising a spray nozzle, dipping bath, pipet, dispenser, needle, catheter, microcatheter, syringe, or auger-shaped member.

12. The water in solvent emulsion of claim 10, wherein said substrate is selected from a group consisting of a medical device, an organ, and a tissue.

13. The water in solvent emulsion of claim 12, wherein said substrate is a medical device.

14. The water in solvent emulsion of claim 13, wherein said medical device is selected from a group consisting of a graft, stent, stent graft, vascular patch, soft tissue patch, heart valve, suture, medical balloon, filter, catheter, and an implantable lead.

15. The water in solvent emulsion of claim 13, wherein said medical device has a single use application.

16. The water in solvent emulsion of claim 10, wherein said emulsion is not stirred or agitated during application onto said substrate.

17. The water in solvent emulsion claim 10, wherein said tetrafluoroethylene copolymer and said water soluble agent are evenly distributed on said substrate.

18. The water in solvent emulsion of claim 1, wherein said water miscible organic solvent is selected from a group consisting of alcohols, esters, ketones, glycols, and aldehydes, and polar aprotic solvents.

19. The water in solvent emulsion of claim 1, wherein said water miscible organic solvent is selected from the group consisting of FDA Class III Solvents.

20. The water in solvent emulsion of claim 1, wherein the emulsion is kinetically stable at 25° C. for at least 5 min without stirring or agitation.

21. The water in solvent emulsion of claim 1, wherein the emulsion is kinetically stable at 25° C. for at least 4 months without stirring or agitation.

22. A coating for a medical device comprising the following components: a tetrafluoroethylene copolymer; a solvent phase comprising a water miscible organic solvent; a water soluble agent; and a water phase, wherein when said components are mixed together, they form an emulsion that is kinetically stable.

23. The coating of claim 22, wherein said tetrafluoroethylene copolymer comprises functional groups selected from a group consisting of acetate, alcohol, amine and amide.

24. The coating of claim 23, wherein said tetrafluoroethylene copolymer is poly(tetrafluoroethylene-co-vinyl acetate) (TFE-VAc).

25. The coating of claim 23, wherein said tetrafluoroethylene copolymer is poly(tetrafluoroethylene-vinyl alcohol) (TFE-co-VOH).

26. The coating of claim 23, wherein said tetrafluoroethylene copolymer is poly(tetrafluoroethylene-co-vinyl alcohol-co-vinyl[aminobutyraldehyde acetal (TFE-VOH-AcAm).

27. The coating of claim 22, wherein said water soluble agent is a therapeutic agent.

28. The coating of claim 27, wherein said therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents;

cell proliferation affectors; vasodilating agents; cilostazol; carvedilol; antibiotics; and combinations thereof.

29. The coating of claim 22, wherein said emulsion is capable of being applied onto a medical device.

30. The coating of claim 29, wherein said emulsion is applied onto said medical device using a single applicator comprises at least one of a spray nozzle, a dipping bath, a pipet, a dispenser, a needle, a catheter, a microcatheter, a syringe, and an auger-shaped member.

31. The coating of claim 29, wherein said emulsion is not stirred or agitated during application onto said medical device.

32. The coating of claim 29, wherein said a tetrafluoroethylene copolymer and said water soluble agent are evenly distributed on said medical device.

33 The coating of claim 29, wherein said medical device is selected from a group consisting of a graft, stent, stent graft, medical balloon, vascular patch, soft tissue patch, heart valve, suture, filter, catheter, and an implantable lead.

34. The coating of claim 29, wherein said medical device has a single use application.

35. The coating of claim 22, wherein said water miscible organic solvent is selected from a group consisting of alcohols, esters, ketone, glycols, and aldehydes, and polar aprotic solvents.

36. A kinetically stable, water in solvent emulsion comprising: an solvent phase comprising a tetrafluoroethylene copolymer and a water miscible organic solvent; an aqueous phase comprising a water soluble agent and water; wherein the ratio of the solvent phase to the aqueous phase is between about 99 to 1 to about 1 to 1.

37. The water in solvent emulsion of claim 36, wherein said tetrafluoroethylene copolymer comprises at least one functional group selected from a group consisting of acetate, alcohol, amine and amide.

38. The water in solvent emulsion of claim 37, wherein said tetrafluoroethylene copolymer is poly(tetrafluoroethylene-co-vinyl acetate) (TFE-VAc).

39. The water in solvent emulsion of claim 37, wherein said tetrafluoroethylene copolymer is poly(tetrafluoroethylene-co-vinyl alcohol) (TFE-VOH).

40. The water in solvent emulsion of claim 37, wherein said tetrafluoroethylene copolymer is poly(tetrafluoroethylene-co-vinyl alcohol-co-vinyl[aminobutyraldehyde acetal (TFE-VOH-AcAm).

41. The water in solvent emulsion of claim 36, wherein said water miscible organic solvent is selected from a group consisting of alcohols, esters, ketone, glycols, and aldehydes, and polar aprotic solvents.

42. The water in solvent emulsion of claim 36, where the ratio of the solvent phase to the aqueous phase is between about 15:1 to about 1:1 by weight.

43. A method for coating a substrate comprising: applying a water in solvent emulsion to said substrate, wherein said water in solvent emulsion comprises; a tetrafluoroethylene copolymer, a solvent phase comprising a water miscible organic solvent, a water soluble agent, a water phase, wherein said emulsion is kinetically stable; and evaporating said miscible organic solvent and water.

44. The method of claim 43, wherein said tetrafluoroethylene copolymer comprises functional groups selected from a group consisting of acetate, alcohol, amine and amide.

45. The method of claim 44, wherein said tetrafluoroethylene copolymer is poly(tetrafluoroethylene-co-vinyl acetate) (TFE-VAc).

46. The method of claim 44, wherein said tetrafluoroethylene copolymer is poly(tetrafluoroethylene-co-vinyl alcohol) (TFE-VOH).

47. The method of claim 44, wherein said tetrafluoroethylene copolymer is poly(tetrafluoroethylene-co-vine alcohol-co-vinyl[aminobutyraldehyde acetal (TFE-VOH-AcAm).

48. The method of claim 43, wherein said substrate is selected from a group consisting of a medical device, an organ, and tissue, and combinations thereof.

49. The method of claim 49, wherein said substrate is a medical device.

50. The method of claim 49, wherein said medical device is selected from the group consisting of a graft, stent, vascular patch, soft tissue patch, heart valve, suture, stent graft, medical balloon, filter, catheter and an implantable lead.

51. The method of claim 49, wherein said medical device has a single use application.

52. The method of claim 49, wherein said emulsion is capable of being applied onto said medical device using a single applicator.

53. The method of claim 52, wherein said single applicator is selected from a group consisting of a spray nozzle, dipping bath, a pipet, a dispenser, a needle, catheter, microcatheter, syringe, and auger-shaped member.

54. The method of claim 43, wherein said emulsion is not stirred or agitated during application onto said substrate.

55. The method of claim 43, wherein said a tetrafluoroethylene copolymer and said water soluble agent are evenly distributed on said substrate.

56. The method of claim 43, wherein said water soluble agent is a therapeutic agent.

57. The method of claim 56, wherein said therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

58. The method of claim 49, wherein said emulsion has been applied to said medical device by at least one of dip coating, pipetting, spraying, and brushing.

59. The method of claim 43, wherein said water miscible organic solvent is selected from a group consisting of alcohols, esters, ketone, glycols, and aldehydes, and polar aprotic solvents.

60. A method of preparing a water in solvent emulsion comprising the steps of: a. dissolving a tetrafluoroethylene copolymer in a water miscible organic solvent; b. dissolving a water soluble agent in water; and c. combining the tetrafluoroethylene copolymer with the water soluble agent, such that the emulsion is kinetically stable.

61. A method of coating a substrate comprising a water-in-solvent emulsion comprising the steps of: a. providing a water in solvent emulsion comprising: a tetrafluoroethylene copolymer, a solvent phase comprising a water miscible organic solvent, a water soluble agent, a water phase, wherein said emulsion is kinetically stable; b. applying the water-in-solvent emulsion to the substrate; and c. and removing the solvent and water.

The method of claim 61, wherein said water soluble agent phase is less than about 500 nm by Raman spectroscopy.

63. A water in solvent emulsion comprising: a tetrafluoroethylene copolymer dissolved in a water miscible organic solvent; a therapeutic agent; and water, wherein the opacity point for the emulsion is greater than 5% water and less than 60% by weight.

64. The water in solvent emulsion of claim 63, wherein said tetrafluoroethylene copolymer comprises a functional group selected from a group consisting of acetate, alcohol, amine, and amide.

65. The water in solvent emulsion of claim 64, wherein said tetrafluoroethylene copolymer is poly(tetrafluoroethylene-co-vinyl acetate) (TFE-VAc).

66. The water in solvent emulsion of claim 64, wherein said tetrafluoroethylene copolymer is poly(tetrafluoroethylene-co-vinyl alcohol) (TFE-VOH).

67. The water in solvent emulsion of claim 64, wherein said tetrafluoroethylene copolymer is poly(tetrafluoroethylene-co-vinyl alcohol-co-vinyl[aminobutyraldehyde acetal (TFE-VOH-AcAm).

68. The water in solvent emulsion of claim 63, wherein said therapeutic agent is a water soluble agent.

69. The water in solvent emulsion of claim 63, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

70. The water in solvent emulsion of claim 63, wherein said therapeutic agent is complexed with a hydrophilic complexing agent to form an inclusion complex.

71. The water in solvent emulsion of claim 70, wherein the inclusion complex consists of a cyclodextrin molecule and a hydrophobic therapeutic agent.

72. The water in solvent emulsion of claim 63, wherein said emulsion is applied onto a substrate.

73. The water in solvent emulsion of claim 72, wherein said emulsion is applied onto said substrate using a single applicator comprising a spray nozzle, dipping bath, pipet, dispenser, needle, catheter, microcatheter, syringe, or auger-shaped member.

74. The water in solvent emulsion of claim 72, wherein said substrate is selected from a group consisting of a medical device, an organ, and a tissue.

75. The water in solvent emulsion of claim 74, wherein said substrate is a medical device.

76. The water in solvent emulsion of claim 75, wherein said medical device is selected from a group consisting of a graft, stent, stent graft, vascular patch, soft tissue patch, heart valve, suture, medical balloon, filter, catheter, and an implantable lead.

77. The water in solvent emulsion of claim 75, wherein said medical device has a single use application.

78. The water in solvent emulsion of claim 72, wherein said emulsion is not stirred or agitated during application onto said substrate.

79. The water in solvent emulsion of claim 72, wherein said a tetrafluoroethylene copolymer and said water soluble agent are evenly distributed on said substrate.

80. The water in solvent emulsion of claim 63, wherein said water miscible organic solvent is selected from a group consisting of alcohols, esters, ketone, glycols, and aldehydes, and polar aprotic solvents.

81. The water in solvent emulsion of claim 63, wherein said water miscible organic solvent is selected from the group consisting of FDA Class III Solvents.

82. The water in solvent emulsion of claim 63, wherein the emulsion is kinetically stable at 25° C. for at least 5 min without stirring or agitation.

83. The water in solvent emulsion claim 63, wherein the emulsion is kinetically stable at 25° C. for at least 4 months without stirring or agitation.

84. A water in solvent emulsion comprising: a tetrafluoroethylene copolymer dissolved in a water miscible organic solvent; and a water soluble agent dissolved in water, wherein the emulsion is kinetically stable.

85. The water in solvent emulsion of claim 84, wherein said tetrafluoroethylene copolymer comprises a functional group selected from a group consisting of acetate, alcohol, amine, and amide.

86. The water in solvent emulsion of claim 85, wherein said tetrafluoroethylene copolymer is poly(tetrafluoroethylene-co-vinyl acetate) (TFE-VAc).

87. The water in solvent emulsion of claim 85, wherein said tetrafluoroethylene copolymer is poly(tetrafluoroethylene-co-vinyl alcohol) (TFE-VOH).

88. The water in solvent emulsion of claim 85, wherein said tetrafluoroethylene copolymer is poly(tetrafluoroethylene-co-vinyl alcohol-co-vinyl[aminobutyraldehyde acetal (TFE-VOH-AcAm).

89. The water in solvent emulsion of claim 84, wherein said water soluble agent is a therapeutic agent.

90. The water in solvent emulsion of claim 89, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

91. The water in solvent emulsion of claim 84, wherein said water soluble agent is an inclusion complex consisting of a hydrophilic complexing agent and a hydrophobic therapeutic agent.

92. The water in solvent emulsion of claim 91, wherein the inclusion complex consists of a cyclodextrin molecule and a hydrophobic therapeutic agent.

93. The water in solvent emulsion of claim 84, wherein said emulsion is applied onto a substrate.

94. The water in solvent emulsion of claim 93, wherein said emulsion is applied to said substrate using a single applicator comprising a spray nozzle, dipping bath, pipet, dispenser, needle, catheter, microcatheter, syringe, or auger-shaped member.

95. The water in solvent emulsion of claim 93, wherein said substrate is selected from a group consisting of a medical device, an organ, and a tissue.

96. The water in solvent emulsion of claim 93, wherein said substrate is a medical device.

97. The water in solvent emulsion of claim 96, wherein said medical device is selected from a group consisting of a graft, stent, stent graft, vascular patch, soft tissue patch, heart valve, suture, medical balloon, filter, catheter, and an implantable lead.

98. The water in solvent emulsion of claim 96, wherein said medical device has a single use application.

99. The water in solvent emulsion of claim 93, wherein said emulsion is not stirred or agitated during application onto said substrate.

100. The water in solvent emulsion of of claim 84, wherein said a tetrafluoroethylene copolymer and said water soluble agent are evenly distributed on said substrate.

101. The water in solvent emulsion of claim 84, wherein said water miscible organic solvent is selected from a group consisting of alcohols, esters, ketone, glycols, and aldehydes, and polar aprotic solvents.

102. The water in solvent emulsion of claim 84, wherein said water miscible organic solvent is selected from the group consisting of FDA Class III Solvents.

103. The water in solvent emulsion of of claim 84, wherein the emulsion is kinetically stable at 25° C. for at least 5 m in without stirring or agitation.

104. The water in solvent emulsion of claim 84, wherein the emulsion is kinetically stable at 25° C. for at least 4 months without stirring or agitation.

105. A water in solvent emulsion comprising: a tetrafluoroethylene copolymer and a hydrophobic agent dissolved in a water miscible organic solvent; and water, wherein the emulsion is kinetically stable.

106. The water in solvent emulsion of claim 105, wherein said tetrafluoroethylene copolymer comprises a functional group selected from a group consisting of acetate, alcohol, amine, and amide.

107. The water in solvent emulsion of claim 106, wherein said tetrafluoroethylene copolymer is poly(tetrafluoroethylene-co-vinyl acetate) (TFE-VAc).

108. The water in solvent emulsion of claim 106, wherein said tetrafluoroethylene copolymer is poly(tetrafluoroethylene-co-vinyl alcohol) (TFE-VOH).

109. The water in solvent emulsion of claim 106, wherein said tetrafluoroethylene copolymer is poly(tetrafluoroethylene-co-vinyl alcohol-co-vinyl[aminobutyraldehyde acetal (TFE-VOH-AcAm).

110. The water in solvent emulsion of claim 105, wherein said hydrophobic agent comprises a therapeutic agent.

111. The water in solvent emulsion of claim 110, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

112. The water in solvent emulsion of claim 105, wherein said hydrophobic agent is an inclusion complex consisting of a hydrophilic complexing agent and a hydrophobic therapeutic agent.

113. The water in solvent emulsion of claim 112, wherein the inclusion complex consists of a cyclodextrin molecule and a hydrophobic therapeutic agent.

114. The water in solvent emulsion of claim 105, wherein said emulsion is applied onto a substrate.

115. The water in solvent emulsion of claim 114, wherein said emulsion is applied to said substrate using a single applicator comprising a spray nozzle, dipping bath, pipet, dispenser, needle, catheter, microcatheter, syringe, or auger-shaped member.

116. The water in solvent emulsion of claim 114, wherein said substrate is selected from a group consisting of a medical device, an organ, and a tissue.

117. The water in solvent emulsion of claim 114, wherein said substrate is a medical device.

118. The water in solvent emulsion of claim 117, wherein said medical device is selected from a group consisting of a graft, stent, stent graft, vascular patch, soft tissue patch, heart valve, suture, medical balloon, filter, catheter, and an implantable lead.

119. The water in solvent emulsion of claim 117, wherein said medical device has a single use application.

120. The water in solvent emulsion of any claim 114, wherein said emulsion is not stirred or agitated during application onto said substrate.

121. The water in solvent emulsion of claim 114, wherein said a tetrafluoroethylene copolymer and said hydrophobic agent are evenly distributed on said substrate.

122. The water in solvent emulsion of claim 105, wherein said water miscible organic solvent is selected from a group consisting of alcohols, esters, ketone, glycols, and aldehydes, and polar aprotic solvents.

123. The water in solvent emulsion of claim 105, wherein said water miscible organic solvent is selected from the group consisting of FDA Class III Solvents.

124. The water in solvent emulsion of claim 105, wherein the emulsion is kinetically stable at 25° C. for at least 5 m in without stirring or agitation.

125. The water in solvent emulsion of claim 105, wherein the emulsion is kinetically stable at 25° C. for at least 4 months without stirring or agitation.

126. A coating for a substrate comprising the following components: a tetrafluoroethylene copolymer; a solvent phase comprising a water miscible organic solvent; a hydrophobic therapeutic agent; a hydrophilic complexing agent; and a water phase wherein when said components are mixed together, they form an emulsion that is kinetically stable.

127. The coating of claim 126, wherein said tetrafluoroethylene copolymer comprises functional groups selected from a group consisting of acetate, alcohol, amine and amide.

128. The coating of claim 127, wherein said tetrafluoroethylene copolymer is poly(tetrafluoroethylene-co-vinyl acetate) (TFE-VAc).

129. The coating of claim 127, wherein said tetrafluoroethylene copolymer is poly(tetrafluoroethylene-vinyl alcohol) (TFE-co-VOH).

130. The coating of claim 127, wherein said tetrafluoroethylene copolymer is poly(tetrafluoroethylene-co-vinyl alcohol-co-vinyl[aminobutyraldehyde acetal (TFE-VOH-AcAm).

131. The coating of claim 126, wherein the coating is applied to a substrate comprising at least one of a medical device and a living tissue.

132. The coating of claim 126, wherein said hydrophobic therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents;

anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

133. The coating of claim 126, wherein said emulsion is capable of being applied onto said substrate using a single applicator.

134. The coating of claim 133, wherein said single applicator comprises at least one of a spray nozzle, a dipping bath, a pipet, a dispenser, a needle, a catheter, a microcatheter, syringe, and an auger-shaped member.

135. The coating of claim 131, wherein said emulsion is not stirred or agitated during application onto said substrate.

136. The coating of claim 131, wherein said a tetrafluoroethylene copolymer and said hydrophobic therapeutic agent are evenly distributed on said substrate.

137. The coating of claim 131, wherein said substrate is at least a portion of a medical device selected from a group consisting of a graft, stent, stent graft, vascular patch, soft tissue patch, heart valve, suture, medical balloon, filter, catheter, and an implantable lead.

138. The coating of claim 131, wherein said substrate is at least a portion of a medical device with a a single use application.

139. The coating of claim 126, wherein said water miscible organic solvent is selected from a group consisting of alcohols, esters, ketone, glycols, and aldehydes, and polar aprotic solvents.

140. A coating for a substrate comprising the following components: a tetrafluoroethylene copolymer; a solvent phase comprising a water miscible organic solvent; a hydrophobic therapeutic agent; and a water phase, wherein when said components are mixed together, they form an emulsion that is kinetically stable.

141. The coating of claim 140, wherein said tetrafluoroethylene copolymer comprises functional groups selected from a group consisting of acetate, alcohol, amine and amide.

142. The coating of claim 141, wherein said tetrafluoroethylene copolymer is poly(tetrafluoroethylene-co-vinyl acetate) (TFE-VAc).

143. The coating of claim 141, wherein said tetrafluoroethylene copolymer is poly(tetrafluoroethylene-vinyl alcohol) (TFE-co-VOH).

144. The coating of claim 141, wherein said tetrafluoroethylene copolymer is poly(tetrafluoroethylene-co-vinyl alcohol-co-vinyl[aminobutyraldehyde acetal (TFE-VOH-AcAm).

145. The coating of claim 140, wherein the coating is applied to a substrate is comprising at least a portion of at least one of a medical device and a living tissue.

146. The coating of claim 140, wherein said hydrophobic therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

147. The coating of claim 145, wherein said emulsion is capable of being applied onto said substrate using a single applicator.

148. The coating of claim 147, wherein said single applicator comprises at least one of a spray nozzle, a dipping bath, a needle, pipet, dispenser, a catheter, a microcatheter, syringe, and an auger-shaped member.

149. The coating of claim 145, wherein said emulsion is not stirred or agitated during application onto said substrate.

150. The coating of claim 145, wherein said a tetrafluoroethylene copolymer and said hydrophobic therapeutic agent are evenly distributed on said substrate.

151. The coating of claim 145, wherein said substrate is at least a portion of a medical device is selected from a group consisting of a graft, stent, stent graft, medical balloon, filter, vascular patch, soft tissue patch, heart valve, suture, catheter, and an implantable lead.

152. The coating of claim 145, wherein said substrate is at least a portion of a medical device with a single use application.

153. The coating of claim 140, wherein said water miscible organic solvent is selected from a group consisting of alcohols, esters, ketone, glycols, and aldehydes, and polar aprotic solvents.

154. A kinetically stable, water in solvent emulsion comprising: a solvent phase comprising a tetrafluoroethylene copolymer and a water miscible organic solvent; an aqueous phase comprising a hydrophobic agent, a hydrophilic complexing agent, and water; wherein the ratio of the solvent phase to the aqueous phase ranges from about 99 to 1 to about 1 to 1.

155. The water in solvent emulsion of claim 154, wherein said tetrafluoroethylene copolymer comprises at least one functional group selected from a group consisting of acetate, alcohol, amine and amide.

156. The water in solvent emulsion of claim 155, wherein said tetrafluoroethylene copolymer is poly(tetrafluoroethylene-co-vinyl acetate) (TFE-VAc).

157. The water in solvent emulsion of claim 155, wherein said tetrafluoroethylene copolymer is poly(tetrafluoroethylene-co-vinyl alcohol) (TFE-VOH).

158. The water in solvent emulsion of claim 155, wherein said tetrafluoroethylene copolymer is poly(tetrafluoroethylene-co-vinyl alcohol-co-vinyl[aminobutyraldehyde acetal (TFE-VOH-AcAm).

159. The water in solvent emulsion of claim 154, wherein said water miscible organic solvent is selected from a group consisting of alcohols, esters, ketone, glycols, and aldehydes, and polar aprotic solvents.

160. The water in solvent emulsion of any claim 154, wherein the ratio of the solvent phase to the aqueous phase is between about 15:1 to about 1:1 by weight.

161. A kinetically stable, water in solvent emulsion comprising: a solvent phase comprising a tetrafluoroethylene copolymer, a hydrophobic agent, and a water miscible organic solvent; and an aqueous phase comprising water; wherein the ratio of the solvent phase to the aqueous phase ranges from about 99 to 1 to about 1 to 1.

162. The water in solvent emulsion of claim 161, wherein said tetrafluoroethylene copolymer comprises at least one functional group selected from a group consisting of acetate, alcohol, amine and amide.

163. The water in solvent emulsion of claim 162, wherein said tetrafluoroethylene copolymer is poly(tetrafluoroethylene-co-vinyl acetate) (TFE-VAc).

164. The water in solvent emulsion of claim 162, wherein said tetrafluoroethylene copolymer is poly(tetrafluoroethylene-co-vinyl alcohol) (TFE-VOH).

165. The water in solvent emulsion of claim 162, wherein said tetrafluoroethylene copolymer is poly(tetrafluoroethylene-co-vinyl alcohol-co-vinyl[aminobutyraldehyde acetal (TFE-VOH-AcAm).

166. The water in solvent emulsion of any claim 161, wherein said water miscible organic solvent is selected from a group consisting of alcohols, esters, ketone, glycols, and aldehydes, and polar aprotic solvents.

167. The water in solvent emulsion of claim 161, where the ratio of the solvent phase to the aqueous phase is between about 15:1 to about 1:1 by weight.

168. A method for coating a substrate comprising: applying a water in solvent emulsion to said substrate, wherein said water in solvent emulsion comprises; a tetrafluoroethylene copolymer, a solvent phase comprising a water miscible organic solvent, a hydrophobic agent and a hydrophilic complexing agent, a water phase, wherein said emulsion is kinetically stable; and evaporating said organic solvent and water.

169. The method of claim 168, wherein said tetrafluoroethylene copolymer comprises functional groups selected from a group consisting of acetate, alcohol, amine and amide.

170. The method of claim 169, wherein said tetrafluoroethylene copolymer is poly(tetrafluoroethylene-co-vinyl acetate) (TFE-VAc).

171. The method of claim 169, wherein said tetrafluoroethylene copolymer is poly(tetrafluoroethylene-co-vinyl alcohol) (TFE-VOH).

172. The method of claim 169, wherein said tetrafluoroethylene copolymer is poly(tetrafluoroethylene-co-vinyl alcohol-co-vinyl[aminobutyraldehyde acetal (TFE-VOH-AcAm).

173. The method of claim 168, wherein said substrate is selected from a group consisting of a medical device, an organ, and tissue.

174. The method of claim 173, wherein said substrate is a medical device.

175. The method of claim 174, wherein said medical device is selected from the group consisting of a graft, stent, stent graft, vascular patch, soft tissue patch, heart valve, suture, medical balloon, filter, catheter and an implantable lead.

176. The method of claim 174, wherein said medical device has a single use application.

177. The method of claim 168, wherein said emulsion is capable of being applied onto a medical device using a single applicator.

178. The method of claim 177, wherein said single applicator is selected from a group consisting of a spray nozzle, dipping bath, pipet, dispenser, needle, catheter, microcatheter, syringe, and auger-shaped member.

179. The method of claim 168, wherein said emulsion is not stirred or agitated during application onto said substrate.

180. The method of claim 168, wherein said a tetrafluoroethylene copolymer and said hydrophobic agent are evenly distributed on said substrate.

181. The method of claim 168, wherein said hydrophobic agent is a therapeutic agent.

182. The method of claim 181, wherein said therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

183. The method of claim 174, wherein said emulsion has been applied to said medical device by at least one of dip coating, pipetting, spraying, and brushing.

184. The method of claim 168, wherein said water miscible organic solvent is selected from a group consisting of alcohols, esters, ketone, glycols, and aldehydes, and polar aprotic solvents.

185. A method for coating a substrate comprising: applying a water in solvent emulsion to said substrate, wherein said water in solvent emulsion comprises; a tetrafluoroethylene copolymer, a solvent phase comprising a water miscible organic solvent, a hydrophobic agent, a water phase, wherein said emulsion is kinetically stable; and evaporating said organic solvent and water.

186. The method of claim 185, wherein said tetrafluoroethylene copolymer comprises functional groups selected from a group consisting of acetate, alcohol, amine and amide.

187. The method of claim 186, wherein said tetrafluoroethylene copolymer is poly(tetrafluoroethylene-co-vinyl acetate) (TFE-VAc).

188. The method of claim 186, wherein said tetrafluoroethylene copolymer is poly(tetrafluoroethylene-co-vinyl alcohol) (TFE-VOH).

189. The method of claim 186, wherein said tetrafluoroethylene copolymer is poly(tetrafluoroethylene-co-vinyl alcohol-co-vinyl[aminobutyraldehyde acetal (TFE-VOH-AcAm).

190. The method of claim 185, wherein said substrate is selected from a group consisting of a medical device, an organ, and tissue.

191. The method of claim 185, wherein said substrate is a medical device.

192. The method of claim 191, wherein said medical device is selected from the group consisting of a graft, stent, stent graft, vascular patch, soft tissue patch, heart valve, suture, medical balloon, filter, catheter and an implantable lead.

193. The method of claim 191, wherein said medical device has a single use application.

194. The method of claim 185, wherein said emulsion is capable of being applied onto a medical device using a single applicator.

195. The method of claim 194, wherein said single applicator is selected from a group consisting of a spray nozzle, dipping bath, pipet, dispenser, needle, catheter, microcatheter, syringe, and auger-shaped member.

196. The method of claim 185, wherein said emulsion is not stirred or agitated during application onto said substrate.

197. The method of claim 185, wherein said a tetrafluoroethylene copolymer and said hydrophobic agent are evenly distributed on said substrate.

198. The method of claim 185, wherein said hydrophobic agent is a therapeutic agent.

199. The method of claim 198, wherein said therapeutic agent is selected from a group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA;

RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

200. The method of claim 191, wherein said emulsion has been applied to said medical device by at least one of dip coating, pipetting, spraying, and brushing.

201. The method of claim 185, wherein said water miscible organic solvent is selected from a group consisting of alcohols, esters, ketone, glycols, and aldehydes, and polar aprotic solvents.

202. A method of preparing a water in solvent emulsion comprising the steps of: a. dissolving a tetrafluoroethylene copolymer in a water miscible organic solvent; b. dissolving a hydrophilic complexing agent and a hydrophobic agent in water; and c. combining the copolymer solution with the complexing agent and the hydrophobic agent, such that the emulsion is kinetically stable.

203. A method of preparing a water in solvent emulsion comprising the steps of: a. dissolving a tetrafluoroethylene copolymer and a hydrophobic agent in a water miscible organic solvent; b. providing water; and c. combining the copolymer and agent solution with the water, such that the emulsion is kinetically stable.

204. A method of coating a substrate comprising a water-in-solvent emulsion comprising the steps of: a. providing a water in solvent emulsion comprising: a tetrafluoroethylene copolymer, a solvent phase comprising a water miscible organic solvent, a hydrophilic complexing agent, a hydrophobic agent, a water phase, wherein said emulsion is kinetically stable; b. applying the emulsion to the substrate; and c. and removing the solvent and water.

205. The method of claim 204, wherein said hydrophobic agent phase is less than 500 nm by Raman spectroscopy.

206. A method of coating a substrate comprising a water-in-solvent emulsion comprising the steps of: a. providing a water in solvent emulsion comprising: a tetrafluoroethylene copolymer, a solvent phase comprising a water miscible organic solvent, a hydrophobic agent, a water phase, wherein said emulsion is kinetically stable; b. applying the emulsion to the substrate; and c. and removing the solvent and water.

207. The method of claim 206, wherein said water soluble agent phase is less than 500 nm by Raman spectroscopy.

208. A coating comprising: a tetrafluoroethylene copolymer mixed with a water soluble agent, wherein the coating has at least a 50% reduction in excess heat capacity on a tetrafluoroethylene copolymer mass basis as compared with a coating of tetrafluoroethylene copolymer with no water soluble agent.

209. The coating of claim 208, wherein the coating has at least a 80% reduction in excess heat capacity on a tetrafluoroethylene copolymer mass basis as compared with a coating of tetrafluoroethylene copolymer with no water soluble agent.

210. The coating of claim 208, wherein said tetrafluoroethylene copolymer comprises a functional group selected from a group consisting of acetate, alcohol, amine, and amide.

211. The coating of claim 208, wherein said tetrafluoroethylene copolymer is poly(tetrafluoroethylene-co-vinyl acetate) (TFE-VAc).

212. The coating of claim 208, wherein said tetrafluoroethylene copolymer is poly(tetrafluoroethylene-co-vinyl alcohol) (TFE-VOH).

213. The coating of claim 208, wherein said tetrafluoroethylene copolymer is poly(tetrafluoroethylene-co-vinyl alcohol-co-vinyl[aminobutyraldehyde acetal (TFE-VOH-AcAm).

214. The coating of 208, wherein said water soluble agent is a therapeutic agent.

215. The coating of claim 214, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

216. A coating comprising: a tetrafluoroethylene copolymer mixed with a water soluble agent, wherein the coating is phase mixed as measured by modulated DSC.

217. The coating of claim 216, wherein the coating has at least a 50% reduction in excess heat capacity on a tetrafluoroethylene copolymer mass basis as compared with a coating of tetrafluoroethylene copolymer with no water soluble agent.

218. The coating of claim 216, wherein said tetrafluoroethylene copolymer comprises a functional group selected from a group consisting of acetate, alcohol, amine, and amide.

219. The coating of claim 216, wherein said tetrafluoroethylene copolymer is poly(tetrafluoroethylene-co-vinyl acetate) (TFE-VAc).

220. The coating of claim 216, wherein said tetrafluoroethylene copolymer is poly(tetrafluoroethylene-co-vinyl alcohol) (TFE-VOH).

221. The coating of claim 216, wherein said tetrafluoroethylene copolymer is poly(tetrafluoroethylene-co-vinyl alcohol-co-vinyl[aminobutyraldehyde acetal (TFE-VOH-AcAm).

222. The coating of 216, wherein said water soluble agent is a therapeutic agent.

223. The coating of claim 222, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

224. The coating of claim 22, wherein the coating has at least a 50% reduction in excess heat capacity on a tetrafluoroethylene copolymer mass basis as compared with a coating of tetrafluoroethylene copolymer with no water soluble agent.

225. The coating of claim 224, wherein the coating has at least a 80% reduction in excess heat capacity on a tetrafluoroethylene copolymer mass basis as compared with a coating of tetrafluoroethylene copolymer with no water soluble agent.

226. The coating of claim 22, wherein the coating is phase mixed as measured by modulated differential scanning calorimetry.

227. The coating claim 22, wherein the coating shows essentially no reversing exotherms and essentially no non-reversing exotherms on a tetrafluoroethylene copolymer mass basis in a first heating run.

228. A water in solvent emulsion comprising: a tetrafluoroethylene copolymer dissolved in a water miscible organic solvent; and a water soluble agent dissolved in water, wherein upon evaporation of water miscible organic solvent and water, the resulting bolus has at least a 50% reduction in excess heat capacity water soluble as compared with a coating of tetrafluoroethylene copolymer with no water soluble agent.

229. The water in solvent emulsion of claim 228, wherein the bolus has at least a 80% reduction in excess heat capacity on a tetrafluoroethylene copolymer mass basis as compared with a bolus of tetrafluoroethylene copolymer with no water soluble agent.

230. The water in solvent emulsion of claim 229, wherein said tetrafluoroethylene copolymer comprises a functional group selected from a group consisting of acetate, alcohol, amine, and amide.

231. The water in solvent emulsion of claim 228, wherein said tetrafluoroethylene copolymer is poly(tetrafluoroethylene-co-vinyl acetate) (TFE-VAc).

232. The water in solvent emulsion of claim 228, wherein said tetrafluoroethylene copolymer is poly(tetrafluoroethylene-co-vinyl alcohol) (TFE-VOH).

233. The water in solvent emulsion of claim 228, wherein said tetrafluoroethylene copolymer is poly(tetrafluoroethylene-co-vinyl alcohol-co-vinyl[aminobutyraldehyde acetal (TFE-VOH-AcAm).

234. The water in solvent emulsion of 228, wherein said water soluble agent is a therapeutic agent.

235. The water in solvent emulsion of claim 234, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

236. A water in solvent emulsion comprising: a tetrafluoroethylene copolymer dissolved in a water miscible organic solvent; and a water soluble agent dissolved in water, wherein upon evaporation of water miscible organic solvent and water, the resulting bolus is phase mixed as measured by modulated differential scanning calorimetry.

237. The water in solvent emulsion of claim 236, wherein the bolus has at least a 50% reduction in excess heat capacity on a tetrafluoroethylene copolymer mass basis as compared with a bolus of tetrafluoroethylene copolymer with no water soluble agent.

238. The water in solvent emulsion of claim 236, wherein said tetrafluoroethylene copolymer comprises a functional group selected from a group consisting of acetate, alcohol, amine, and amide.

239. The water in solvent emulsion of claim 236, wherein said tetrafluoroethylene copolymer is poly(tetrafluoroethylene-co-vi nyl acetate) (TFE-VAc).

240. The water in solvent emulsion of claim 236, wherein said tetrafluoroethylene copolymer is poly(tetrafluoroethylene-co-vinyl alcohol) (TFE-VOH).

241. The water in solvent emulsion of claim 236, wherein said tetrafluoroethylene copolymer is poly(tetrafluoroethylene-co-vinyl alcohol-co-vinyl[aminobutyraldehyde acetal (TFE-VOH-AcAm).

242. The water in solvent emulsion of 236, wherein said water soluble agent is a therapeutic agent.

243. The water in solvent emulsion of claim 242, wherein said therapeutic agent is selected from the group consisting of contrast agents; proteins and peptides; anti-coagulants; vascular cell growth inhibitors; analgesics; antibiotics; anti-inflammatory agents; mammalian cells; eukaryotes; prokaryotes; somatic cells; germ cells; erythrocytes; platelets; viruses; prions; DNA; RNA vectors; cellular fractions; mitochondria; anti-neoplastic agents; antiproliferative agents; anti-mitotic agents; anesthetic agents; prostaglandin inhibitors; platelet inhibitors; cytotoxic agents; paclitaxel; sirolimus; cytostatic agents; cell proliferation affectors; vasodilating agents; cilostazol; carvedilol; antibiotics; and combinations thereof.

244. The water in solvent emulsion of claim 1, wherein upon evaporation of water miscible organic solvent and water, the resulting bolus has at least a 50% reduction in excess heat capacity on a tetrafluoroethylene copolymer mass basis as compared with a bolus of tetrafluoroethylene copolymer with no water soluble agent.

245. The coating of claim 224, wherein upon evaporation of water miscible organic solvent and water, the resulting bolus has at least a 80% reduction in excess heat capacity on a tetrafluoroethylene copolymer mass basis as compared with a bolus of tetrafluoroethylene copolymer with no water soluble agent.

246. The coating of claim 1, wherein upon evaporation of water miscible organic solvent and water, the resulting bolus is phase mixed as measured by modulated differential scanning calorimetry.

247. The coating of claim 1, wherein upon evaporation of water miscible organic solvent and water, the resulting bolus shows essentially no reversing exotherms on a tetrafluoroethylene copolymer mass basis and essentially no non-reversing exotherms on a tetrafluoroethylene copolymer mass basis in a first heating run as measured by modulated differential scanning calorimetry.

What is claimed is:

1. A method comprising:
   providing a composition comprising a fluorinated copolymer dissolved in an organic solvent, the fluorinated copolymer comprising tetrafluoroethylene and at least one functional group selected from the group consisting of acetate, alcohol, amine, and amide;
   introducing the composition into a patient; and
   hardening the fluorinated copolymer in the patient by diffusing the organic solvent into the patient.

2. The method of claim 1, wherein the composition is introduced into an occlusion site or a bulking site of the patient.

3. The method of claim 1, wherein the introducing step is performed using a needle, a catheter, or a syringe.

4. The method of claim 1, wherein the hardened fluorinated copolymer is porous.

5. The method of claim 1, wherein the organic solvent is selected from the group consisting of acetic acid, acetone, 1-butanol, 2-butanol, butyl acetate, dimethyl sulfoxide, ethanol, ethyl acetate, ethyl formate, formic acid, isobutyl acetate, isopropyl acetate, methyl acetate, 3-methyl-1-butanol, methylethyl ketone, methylisobutyl ketone, 2-methyl-1-propanol, 1-pentanol, 1-propanol, 2-propanol, propyl acetate, methyl acetate, propylene glycol, acetonitrile, dioxane, formamide, dimethylformamide, pyridine, n-Methyl-2-pyrrolidone, methylpyrrolidone, dimethylacetamide, ethylene glycol, methyoxymethanol, pyridine, piperidine, sulfolane, tetrahydrofuran, trichloroacetic acid, polyethylene glycol, and polyethylene oxide.

6. The method of claim 1, wherein the introducing step comprises filling an occlusive casing with the composition.

7. The method of claim 1, wherein the fluorinated copolymer is poly(tetrafluoroethylene-co-vinyl alcohol) (TFE-VOH).

\* \* \* \* \*